(12) United States Patent
Lepine et al.

(10) Patent No.: US 8,382,687 B2
(45) Date of Patent: Feb. 26, 2013

(54) METHOD FOR DETERMINING THE BIOLOGICAL AGE OF A COMPANION ANIMAL

(75) Inventors: Allan John Lepine, Dayton, OH (US); Dennis Richard Ditmer, Springboro, OH (US); Lori Lee Halsey, Brookville, OH (US); John Russell Burr, Clay Township, OH (US)

(73) Assignee: The IAMS Company, Cincinnati, OH (US)

( * ) Notice: Subject to any disclaimer, the term of this patent is extended or adjusted under 35 U.S.C. 154(b) by 107 days.

(21) Appl. No.: 12/395,924

(22) Filed: Mar. 2, 2009

(65) Prior Publication Data

US 2010/0222709 A1 Sep. 2, 2010

(51) Int. Cl.
*A61B 5/103* (2006.01)
*A61B 5/107* (2006.01)
*A61B 5/11* (2006.01)

(52) U.S. Cl. .......... 600/595; 600/587; 600/592; 119/72

(58) Field of Classification Search .................. 600/587, 600/592, 595; 119/712
See application file for complete search history.

(56) References Cited

U.S. PATENT DOCUMENTS

| | | | |
|---|---|---|---|
| 4,195,643 A * | 4/1980 | Pratt, Jr. .......................... | 600/592 |
| 4,631,676 A | 12/1986 | Pugh | |
| 4,813,436 A | 3/1989 | Au | |
| 5,138,550 A * | 8/1992 | Abraham et al. .......... | 340/573.7 |
| 5,930,741 A | 7/1999 | Kramer | |
| 5,952,585 A | 9/1999 | Trantzas et al. | |
| 6,231,527 B1 | 5/2001 | Sol | |
| 6,234,982 B1 | 5/2001 | Arvin | |
| 6,699,207 B2 * | 3/2004 | Tasch et al. .................... | 600/587 |
| 6,836,744 B1 | 12/2004 | Asphahani et al. | |
| 6,895,341 B2 | 5/2005 | Barrey et al. | |
| 7,089,151 B2 * | 8/2006 | Batterman et al. ............ | 702/181 |
| 7,273,453 B2 * | 9/2007 | Shallenberger ............... | 600/300 |
| 7,368,481 B1 * | 5/2008 | Rapisarda ...................... | 514/783 |
| RE40,427 E * | 7/2008 | Nashner ......................... | 600/595 |
| 7,467,603 B2 * | 12/2008 | Davies ........................... | 119/712 |
| 7,527,023 B2 * | 5/2009 | Davies ........................... | 119/712 |
| 7,580,798 B2 * | 8/2009 | Brunner et al. .................. | 702/19 |
| 7,627,451 B2 * | 12/2009 | Vock et al. ..................... | 702/178 |
| 7,650,204 B2 * | 1/2010 | Dariush ......................... | 700/245 |
| 7,673,587 B2 * | 3/2010 | Davies ........................... | 119/712 |
| 7,736,273 B2 * | 6/2010 | Cox et al. ........................... | 482/8 |
| 2004/0158174 A1 * | 8/2004 | Tasch et al. .................... | 600/587 |
| 2005/0001768 A1 | 1/2005 | Sekiguchi et al. | |
| 2005/0004495 A1 | 1/2005 | Goswami | |
| 2005/0015002 A1 | 1/2005 | Dixon et al. | |
| 2005/0228239 A1 * | 10/2005 | Shallenberger ............... | 600/300 |

(Continued)

FOREIGN PATENT DOCUMENTS

WO WO 01/91640 A1 12/2001
WO WO 2004/092744 A2 10/2004

(Continued)

*Primary Examiner* — Sean Dougherty
(74) *Attorney, Agent, or Firm* — Amy M. Foust; Adam W. Borgman

(57) ABSTRACT

A method for determining the biological age of the companion animal. A companion animal ambulates from a first region to a second region of a pressure detection unit and the footfall data is utilized in the determination of the biological age of the companion animal.

19 Claims, 16 Drawing Sheets

U.S. PATENT DOCUMENTS

| | | | |
|---|---|---|---|
| 2006/0000420 A1* | 1/2006 | Davies | 119/174 |
| 2006/0270950 A1* | 11/2006 | Dariush | 601/5 |
| 2006/0293613 A1 | 12/2006 | Fatehi et al. | |
| 2007/0021689 A1 | 1/2007 | Stergiou et al. | |
| 2007/0130893 A1* | 6/2007 | Davies | 54/1 |
| 2007/0204801 A1* | 9/2007 | Davies | 119/712 |
| 2007/0204802 A1* | 9/2007 | Davies | 119/712 |
| 2008/0009772 A1* | 1/2008 | Tyler et al. | 600/595 |
| 2008/0175443 A1* | 7/2008 | Kahn et al. | 382/115 |
| 2008/0191864 A1* | 8/2008 | Wolfson | 340/524 |
| 2009/0027196 A1* | 1/2009 | Schoettle | 340/541 |
| 2010/0222709 A1* | 9/2010 | Lepine et al. | 600/595 |

FOREIGN PATENT DOCUMENTS

WO    WO 2005/001768 A1    1/2005

* cited by examiner

METHOD FOR DETERMINING THE BIOLOGICAL AGE OF A COMPANION ANIMAL

FIELD OF THE INVENTION

The present invention relates to determining the biological age of a companion animal. The biological age is determined through observation of the mobility of the companion animal as the companion animal ambulates across a pressure detection unit. This invention further is related to providing a recommendation for a management program for companion animal health care, well-being and nutrition.

BACKGROUND OF THE INVENTION

An increasing number of people are acquiring and caring for a great variety of companion animals. Many companion animal breeders, owners, and caregivers would like their companion animals to live longer and healthier lives. Breeders, owners, and caregivers of these companion animals have a desire to understand the physical and biological attributes, genetic makeup, heritable disease, disorder background, and longevity of their companion animals. While companion animals and other animals generally live longer and have a better quality of life today due to improved nutrition and medical care, substantial investments in time, effort and financial resources are made to characterize the health state of those companion animals. There is also a desire to conduct periodic health assessments of those companion animals.

It would be of value to provide a method for assessing the health of a companion animal. There are many indicators of health and wellness in companion animals, including markers such as biomarkers, behavioral indicators, biometrics, etc. An example of an indicator of the health and wellness of a companion animal is the mobility of the companion animal. A companion animal may have an expected mobility based on the companion animal's chronological age but the actual mobility of the companion animal may vary from the expected mobility as the companion animal ages. This variance may be a result of any number of factors, such as, but not limited to, activity level, weight management, disease, arthritic conditions, etc. The observation of the actual mobility of the companion animal can be utilized in determining the biological age of the companion animal. A disparity between the chronological age and biological age can be an indicator of the health and wellness of the companion animal. It would be helpful to develop an individualized management program recommendation for the companion animal. Such a management program can maintain, enhance or improve the companion animal's biological age through dietary modification, supplement administration, weight loss/management plans, physical activity recommendations, veterinary intervention and combinations thereof. The maintenance, enhancement and/or improvement of the biological age of the companion animal may be assessed and/or documented through caregiver perception, veterinary assessment, and/or subsequent determinations of biological age. It would be beneficial to provide a method for assessing the impact of the management program on the biological age of the companion animal.

SUMMARY OF THE INVENTION

A method of determining a companion animal's biological age, said method comprising the steps of providing at least one pressure detection unit having one or more pressure sensors; ambulating the companion animal from a first region of the pressure detection unit to a second region of the pressure detection unit to collect footfall data; analyzing the footfall data to convert the footfall data into movement data which is utilized in a biological age equation from a representative class of animals to determine a biological age for the companion animal.

A method for evaluating a companion animal's biological age with respect to a biological age of a representative class of animals, the method comprising the steps of providing at least one pressure detection unit comprising one or more pressure sensors; ambulating the companion animal from a first region of the pressure detection unit to a second region of the pressure detection unit to collect footfall data; analyzing the footfall data to convert the footfall data into movement data which is utilized in a biological age equation from a representative class of animals to determine a biological age of the companion animal; and comparing the biological age of the companion animal to an average biological age of said representative class of animals.

A database comprising a biological age of at least one companion animal, said biological age determined by a method comprising the steps of providing at least one pressure detection unit comprising one or more pressure sensors; ambulating the companion animal from a first region of the pressure detection unit to a second region of the pressure detection unit to collect footfall data; analyzing the footfall data to convert the footfall data into movement data which is utilized in a biological age equation from a representative class of animals to determine a biological age of the companion animal; and storing the biological age in the database.

DETAILED DESCRIPTION OF THE INVENTION

Figure 1:
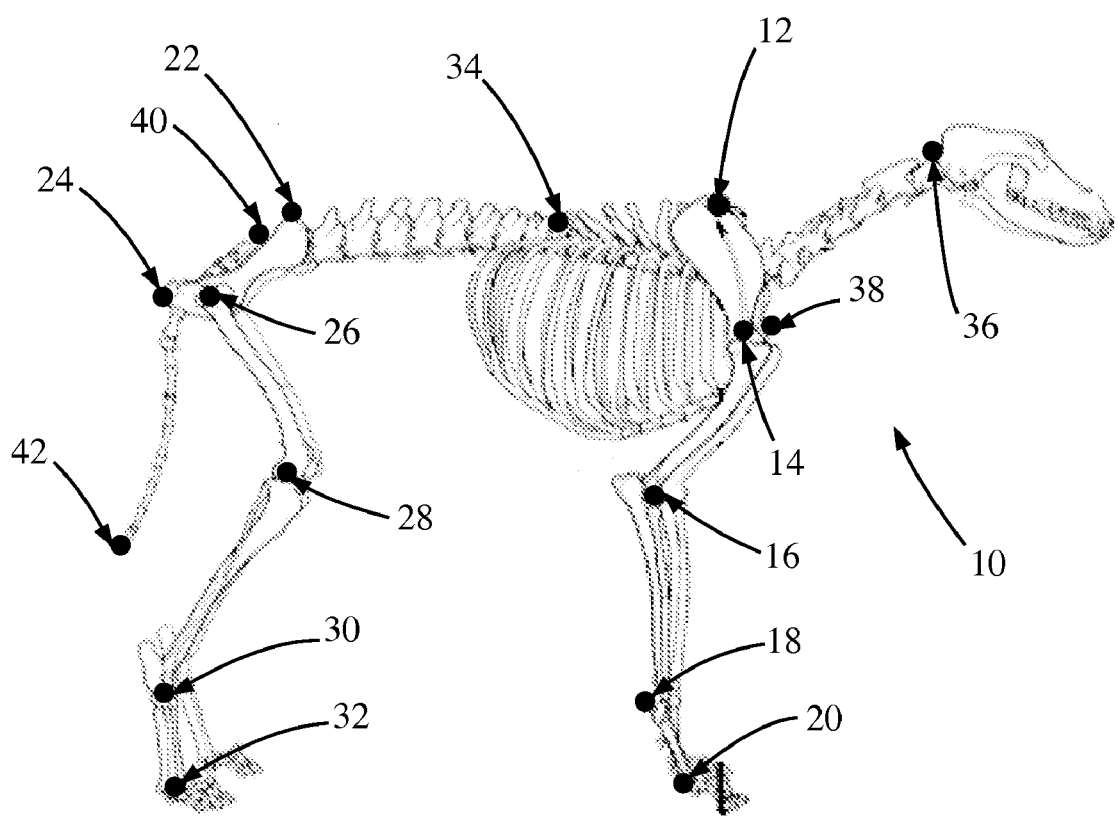
FIG. 1 is an illustration of the points of measurement during the collection of conformation data of a companion animal such as a dog.

As used herein, the term "biological age" refers to the computed age of a companion animal as determined through the observation, as defined herein, of the mobility of the companion animal. Factors that may affect biological age include, but are not limited to, changes in the physical structure of the body, changes in metabolic processes, changes in motor skill performance, changes in overall health status and combinations thereof. As discussed herein, biological age is expressed on a time scale of years.

As used herein, the term "chronological age" refers to the age of the companion animal measured on a time scale beginning from the companion animal's birth. As discussed herein, chronological age is expressed on a time scale of years (e.g., 6 months is converted to 0.5 years).

As used herein, the term "class of animals" refers to a generalized or more specific categorization of animals. Categorizations include, but are not limited to, breed, characteristics for which breeds were originally developed (e.g, sporting, hound, working, terrier, toy, non-sporting, herding, or other), body size, conformation characteristics, chronological age, naturally occurring gait pattern, physical ailment, and combinations thereof. The class of animals may include purebred animals, cross-bred animals, and combinations thereof.

As used herein, the term "companion animal" refers to domestic animals such as dogs and cats. The companion animal may be a purebred animal or cross-bred animal.

As used herein, the term "conformation data" refers to data measured from the body of the companion animal.

As used herein, the term "footfall data" refers to the footfall pressure and the temporal and spatial parameters of each footfall of an animal as the animal ambulates from a first region of a pressure detection unit to a second region of the pressure detection unit. Footfall data is analyzed to convert the footfall data to movement data.

As used herein, the term "footfall pressure" refers to the pressure exerted by each footfall of an animal on a pressure detection unit as the animal ambulates from a first region of the pressure detection unit to a second region of the pressure detection unit.

As used herein, the term "medical history" refers to historical health data, nutritional history, surgeries, medicines, disease conditions, physical ailments, and combinations thereof of an animal.

As used herein, the term "movement data" refers to the calculated results from the analysis and conversion of footfall data. Movement data includes, but is not limited to, number of pressure sensors activated in a given paw placement, pressure peak (maximum amount of pressure in the series of steps of all four feet), pressure mean (average pressure of the four limbs), pressure time (the time, in seconds, of contact minus the stance time), step length (the distance, in centimeters, between the paw contact of one side of the body and the paw contact of the contra lateral side), stride length (distance, in centimeters, from the farthest hind point of paw to same point of next step), step time (time, in seconds, to complete the distance between the paw contact of one side of the body and the paw contact of the contra lateral side), stride time (time, in seconds, elapsed between the paw going down and the pawing going up), swing time (time, in seconds, elapsed between the paw going up and the paw going down), stance time (the time, in seconds, the paw is on the ground in seconds), distance (total distance covered measured in centimeters), ambulation time (total time, in seconds, the companion animal is on the pressure detection unit from the first step to the last pressure contact), velocity (distance covered in the ambulation divided by time, in centimeters per second), step count (number of steps taken), cadence (pattern of steps taken), step time of all four paws (the time, in seconds, to complete the distance between the paw contact of one side of the body and the paw contact of the contra lateral side (either front or hind)), step length measured individually on each leg (distance, in centimeters, between the contact of the front or hind leg and the contact of its contra lateral leg measured in centimeters), cycle time measured individually for each leg (the time, in seconds, elapsed for swing and stance phase combined), stride length measured individually for each leg (length of step, in centimeters, from toe off to contact for an individual leg), stride velocity measured individually on each leg (stride length covered in a cycle time, centimeters per second), swing percentage of cycle measured individually for each leg (percentage of time an individual limb is in motion and not in stationary phase), swing time measured individually for each leg (time, in seconds, limb is in air or swinging (from toe off to contact)), stance percentage of cycle measured individually for each leg (percentage of time limb is stationary in the cycle relative to the swing phase (contact toe off)), stance time, in seconds, measured individually for each leg, number of sensors measured individually for each leg (number of sensors for an individual leg), peak pressure measured individually for each leg, mean pressure measured individually for each leg, center of gravity (line of movement from the center of gravity of the subject, and combinations thereof.

As used herein, the term "observed" or "observation" refers to measuring the mobility of an animal through mechanical analysis done by a pressure detection unit.

A pressure detection unit is utilized in the observation of the mobility of a companion animal. The companion animal ambulates from a first region of a pressure detection unit to a second region of the pressure detection unit. As the companion animal ambulates from the first region to the second region, each footfall of the companion animal exerts a pressure onto the pressure detection unit. The pressure detection unit records the footfall pressure as well as additional footfall data such as the temporal and spatial parameters of each footfall. The footfall data is analyzed and converted into movement data. The movement data of the companion animal is inserted into a biological age equation developed form the movement data of a representative class of companion animals.

In an embodiment, the footfall data from a representative class of animals is collected, analyzed and converted into movement data. A representative class of animals may be categorized by type, breed, body size, conformation, physical ailment, chronological age, and combinations thereof. Table 1 represents an example of categorizations based on body size and breed. An example of chronological age categorization is less than 4 years, from 5 to 6 years, from 7 to 9 years, and greater than 10 years of age. Non-limiting examples of a comparison between a companion animal and a representative class of animals include comparing the companion animal to a representative class of animals which are the same breed as the companion animal, comparing the companion animal to a representative class of animals which are the same body size (e.g., large breed, medium breed, small breed), comparing the companion animal to a representative class of animals which have the same known or suspected physical ailment and comparing the companion animal to a representative class of animals which have common movement characteristics.

sentative class of animals against which a companion animal with a known or suspected physical ailment may be compared. The comparison of a companion animal with a known or suspected physical ailment to a representative class of animals without a physical ailment can provide for the development of a management program to improve the physical condition of the companion animal. In an embodiment, the representative class of animals may comprise animals with a known physical ailment, such as, for example, osteo-arthritis, and may form a representative class of animals against which a companion animal with the same physical ailment, such as, for example, osteo-arthritis, may be compared. The comparison of a companion animal with a known physical ailment to a representative class of animals with the same known physical ailment allows for the development of a management program to improve the physical condition of the companion animal.

The footfall data of each animal in the representative class of animals is collected and analyzed to convert the footfall data into the movement data described above. The movement

TABLE 1

| Size | Breed |
| --- | --- |
| Extra Large | Anatolian Shepherd Dog, Bernese Mountain Dog, Black Russian Terrier, Borzoi, Bouvier des Flandres, Bullmastiff, Great Dane, Great Pyrenees, Greater Swiss Mountain Dog, Irish Wolfhound, Kuvasz, Mastiff, Mastiff Scottish Deerhound, Neapolitan Mastiff, Newfoundland, Saint Bernard, Scottish Deerhound |
| Large | Afghan Hound, Akita, Alaskan Malamute, American English Coonhound, American Foxhound, Beauceron, Belgian Malinois, Belgian Sheepdog, Belgian Tervuren, Black and Tan Coonhound, Bloodhound, Bluetick Coonhound, Boxer, Briard, Canaan Dog, Chesapeake Bay Retriever, Collie, Curly-Coated Retriever, Doberman Pinscher, Dogue de Bordeaux, English Setter, Flat-Coated Retriever Pointer, German Shepherd Dog, German Shorthaired Pointer, German Wirehaired Pointer, Giant Schnauzer, Golden Retriever, Gordon Setter, Greyhound, Ibizan Hound, Irish Red and White Setter, Irish Setter, Irish Water Spaniel, Komondor, Labrador Retriever, Old English Sheepdog, Otterhound, Pharaoh Hound, Plott, Pointer, Redbone Coonhound, Rhodesian Ridgeback, Rottweiler, Saluki, Spinone Italiano, Tibetan Mastiff, Treeing Walker Coonhound, Vizsla, Weimaraner, Wirehaired Pointing Griffon |
| Medium | Airedale Terrier, American Eskimo Dog, American Staffordshire Terrier, American Water Spaniel, Australian Cattle Dog, Australian Shepherd, Bearded Collie, Border Collie, Boykin Spaniel, Brittany, Chinese Shar-Pei, Chow Chow, Clumber Spaniel, Dalmatian, English Foxhound, English Springer Spaniel, Field Spaniel, Finnish Spitz, German Pinscher, Harrier, Irish Terrier, Keeshond, Kerry Blue Terrier, Norwegian Buhund, Norwegian Elkhound, Nova Scotia Duck Tolling Retriever, Polish Lowland Sheepdog, Portuguese Water Dog, Puli, Pyrenean Shepherd, Samoyed, Siberian Husky, Soft Coated Wheaten Terrier, Standard Poodle, Standard Schnauzer, Welsh Springer Spaniel, Whippet |
| Small | Basenji, Basset Hound, Beagle, Bedlington Terrier, Border Terrier, Boston Terrier, Bull Terrier, Bulldog, Cavalier King Charles Spaniel, Chinese Crested, Cocker Spaniel, Dachshund, English Cocker Spaniel, French Bulldog, Glen of Imaal Terrier, Italian Greyhound, Lakeland Terrier, Löwchen, Miniature Bull Terrier, Miniature Poodle, Miniature Schnauzer, Parson Russell Terrier, Petit Basset Griffon, Vendéen, Pug, Schipperke, Shetland Sheepdog, Shiba Inu, Smooth Fox Terrier, Staffordshire Bull Terrier, Sussex Spaniel, Swedish Vallhund, Tibetan Terrier, Welsh Terrier, Wire Fox Terrier |
| Extra Small | Affenpinscher, Australian Terrier, Bichon Frise, Brussels Griffon, Cairn Terrier, Cardigan Welsh Corgi, Chihuahua, Dandie Dinmont Terrier, English Toy Spaniel, Havanese, Japanese Chin, Lhasa Apso, Maltese, Manchester Terrier, Miniature Pinscher, Norfolk Terrier, Norwich Terrier, Papillon, Pekingese, Pembroke Welsh Corgi, Pomeranian, Scottish Terrier, Sealyham Terrier, Shih Tzu, Silky Terrier, Skye Terrier, Tibetan Spaniel, Toy Fox Terrier, Toy Poodle, West Highland White Terrier, Yorkshire Terrier |

The representative class of animals may comprise animals with no known physical ailments, with known physical ailments and combinations thereof. In an embodiment, the representative class of animals comprises animals without any known physical ailments and provides a representative class of animals against which a companion animal without any known physical ailments may be compared. In an embodiment, the representative class of animals comprises animals without any known physical ailments and provides a repredata of the class of animals is stored in a database. The analysis of the footfall data includes any mathematical manipulation necessary to convert the footfall data per foot, per limb, or per motion into the desired movement data. The movement data of each animal within the representative class of animals is utilized in the development of biological age equations. In an embodiment, the development of biological age equations utilizes statistical analysis such as the Principal Component Method which is a known statistical analysis method. The Principal Component Method utilizes all pieces of movement data to create a covariance matrix and to determine the eigenvectors. An 80% threshold is used throughout the Principal Component Method. The principal components are the linear combinations of the movement data and the interpretation of the principal components relies on the weight (the direction and magnitude) of the movement date. All pieces of movement data are mean-centered and scaled by standard deviation. A stepwise discriminate analysis is used to select a subset of principal components that are statistically significant in discriminating chronological age groups (p-value <0.05). The selected subset of principal components are used in a regression model (linear regression and age regression) to develop biological equations. As different chronological age groups correlate with different subsets of principal components, biological age equations are developed for each subset of principal components. In an embodiment, the following are exemplary chronological age groups: less than four years of age, from 5-6 years of age, from 7-9 years of age, and greater than 10 years of age. The biological age equations are used in the determination of the biological age of a companion animal. In the determination of the biological age of a companion animal, the movement data of the companion animal is inserted into a biological age equation which has been categorized into a chronological age group that corresponds to the chronological age of the companion animal.

In an embodiment, the footfall data from a companion animal is collected, analyzed and converted into movement data. To determine the biological age of the companion animal, the movement data is inserted into a biological age equation from a representative class of animals that has been categorized into a chronological age group that corresponds to the chronological age of the companion animal. The biological age, as expressed in a time scale of years, can then be compared to the chronological age of the companion animal. The comparison of the biological age of the companion animal to the chronological age of the companion animal provides an indication as to whether the biological age of the companion animal is better than, worse than, or the same as the chronological age of the companion animal. The comparison, therefore, is an indication of the health of the companion animal. In an embodiment, the biological age of the companion animal may be compared to the average biological age of the representative class of animals. The comparison of the biological age of the companion animal to the average biological age of the representative class of animals provides an indication as to whether the biological age of the companion animal is better than, worse than or the same as the average biological age of the representative class of animals. The comparison, therefore, is an indication of the health of the companion animal.

In an embodiment, a database stores the footfall data, movement data, biological ages, biological age equations, and combinations thereof of the representative class of animals. In an embodiment, a database stores the footfall data, movement data, biological age and combinations thereof of the companion animal being evaluated.

A pressure detection unit may be portable or may be fixed in place. The pressure detection unit may be located in any environment such as, but not limited to, a home environment, a veterinary clinic, a laboratory setting, a research environment, a breeder environment, a kennel, or a retail environment. The companion animal may present with a known or suspected physical ailment, such as may be the situation in a clinical setting, or the companion animal may present with no physical ailment.

A single pressure detection unit or multiple pressure detection units may be utilized in the observation of the mobility of a companion animal. In an embodiment a pressure detection unit is utilized to collect the footfall data of a companion animal ambulating on a flat surface. In an embodiment, a pressure detection unit is placed on a ramp to collect the footfall data of a companion animal moving up the incline of the ramp, down the decline of the ramp, and combinations thereof. In an embodiment, a pressure detection unit is placed on an elevated surface to collect the footfall data of a companion animal that has jumped onto the elevated surface. In an embodiment, two pressure detection units can be placed end to end to lengthen the area upon which the companion animal ambulates. A pressure detection unit may comprise multiple sections. The multiple sections may be separate from each other. In an embodiment, a pressure detection unit comprises multiple sections which are sized and placed on a set of stairs to collect the footfall data of a companion animal moving up or down the stairs. It is believed that placing the pressure detection unit on surfaces such as, but not limited to, inclines, declines, elevated surfaces, and stairs, allows for the observation of the mobility of the companion animal during a movement normally engaged in by the companion animal and allows for an understanding of what movement affects the mobility of the companion animal. In an embodiment, in determining the biological age of a companion animal, the movement data of the companion animal is inserted into the biological age equation developed following movement by a representative class of animals on a surface the same as or similar to the surface upon which the companion animal ambulated and which has been categorized into a chronological age group that corresponds to the chronological age of the companion animal. For example, in such an embodiment, the movement data of a companion animal that has ambulated up a flight of stairs may be inserted into a biological age equation developed following movement of a representative class of animals up a flight of stairs and which has been categorized into a chronological age group that corresponds to the chronological age of the companion animal.

In an embodiment, an image collector is utilized in association with a pressure detection unit to collect images of the companion animal ambulating from a first region of the pressure detection unit to a second region of the pressure detection unit. The image collector may collect images of the companion animal before, during, and/or after the companion animal ambulates from the first region to the second region of the pressure detection unit. The collected images may be utilized to verify the footfalls of the companion animal. The image collector may be any device that can collect images of the companion animal such as, but not limited to, camera, video camera, video recorder, digital media device and combinations thereof. The image collector may be hand-held, mounted (i.e, on a stand or wall), and combinations thereof.

In an embodiment, the pressure detection unit is utilized in combination with kinematics sensors that have been placed on the body of the companion animal during the collection of footfall data of the companion animal. The kinematics sensors may be placed on locations of the body of the companion animal including, for example, the front and hind legs of the companion animal. The data collected from the kinematics sensors may illustrate the motion of the extremities of the companion animal as the companion animal ambulates from a first region to a second region of the pressure detection unit. The kinematics data may be combined with the footfall data for an overall assessment of the whole body motion of the companion animal.

In an embodiment, the pressure detection unit is associated with a load cell to calculate the weight of the companion animal. In an embodiment, a portion of the pressure detection unit comprises the load cell. For example, a region of the pressure detection unit upon which the companion animal will step may comprise a load cell. In an embodiment, the load cell is separate from the pressure detection unit. In such an embodiment, the companion animal may be weighed prior to or after ambulating from a first region to a second region of the pressure detection unit.

The determination of the biological age of a companion animal includes the observation of the mobility of the companion animal as the companion animal ambulates from a first region of a pressure detection unit to a second region of the pressure detection unit. In an embodiment, the companion animal ambulates from a first region to a second region of a pressure detection unit at a pace that is normal for the companion animal. In an embodiment, the companion animal is guided from a first region to a second region of the pressure detection unit at a particular pace. The pace of the companion animal may be a pace exemplified by a walk, trot, run, and combinations thereof. The pace of the movement may be constant, accelerate, decelerate, and combinations thereof. In an embodiment it may be desirable for the companion animal to ambulate from a first region to a second region of the pressure detection unit at a particular pace to gather desired footfall data. For example, a companion animal may need to ambulate at a pace of a run in order for a health symptom to appear that would not normally appear if the companion animal were to ambulate at a slower pace.

In an embodiment, the companion animal ambulates from a first region of the pressure detection unit to a second region of the pressure detection unit without assistance and/or guidance. It is believed that the lack of assistance and/or guidance will allow for natural movement of the companion animal and therefore will allow for the collection of footfall data that is consistent with the mobility of the companion animal. In an embodiment, the companion animal ambulates from a first region of a pressure detection unit to a second region of the pressure detection unit with assistance and/or guidance. Such assistance or guidance may include, but is not limited to, a handler, treat, leash, guide wall, tunnel, voice commands, hand signals, and combinations thereof. The assistance or guidance may help the companion animal remain on the pressure detection unit for the duration of the movement across the pressure detection unit.

As the companion animal ambulates from a first region of the pressure detection unit to a second region of the pressure detection unit, the footfall pressure of the companion animal is detected by pressure sensor matrices within the pressure detection unit, described below. The companion animal ambulates from a first region of the pressure detection unit to a second region of the pressure detection unit in a forward line of progression that is normal for the companion animal which may include, but is not limited to, a straight line, a diagonal line, weaving, at an angle, and combinations thereof. In an embodiment, the footfalls of the companion animal occur in the normal pattern of the companion animal. In an embodiment in which a companion animal has a known or suspected physical ailment, the footfalls occur in the pattern in which the companion animal accommodates the known or suspected physical ailment.

In the collection of footfall data of the companion animal, the companion animal completes at least one gait cycle during ambulation from a first region to a second region of the pressure detection unit. A gait cycle includes the stance and swing phase of each limb of the companion animal. In an embodiment, the companion animal completes one gait cycle. In an embodiment, the companion animal completes at least two gait cycles. In an embodiment, the companion animal completes at least 1, 2, 3 or 4 gait cycles. In an embodiment, the companion animal completes from 1, 2, 3, or 4 gait cycles to 7, 8, 9 or 10 gait cycles.

The companion animal ambulates from a first region of the pressure detection unit to a second region of the pressure detection unit in at least one repetition. In an embodiment in which the companion animal ambulates across the pressure detection unit, but at least one footfall is unaccounted for, it may be necessary for additional repetitions to occur. In an embodiment in which the companion animal strays from the pressure detection unit during the collection of footfall data, it may be necessary for additional repetitions to occur. In an embodiment, it may be desirable for the companion animal to complete multiple repetitions. In such an embodiment, the multiple repetitions may illustrate consistency in the ambulation of the companion animal from a first region to a second region of the pressure detection unit. In an embodiment in which the companion animal completes multiple repetitions, the movement data from each of the repetitions may be averaged together to obtain a single set of movement data for use in the determination of the biological age of the companion animal. The companion animal may complete at least 1, 2, 3, 4, or 5 repetitions. The companion animal may complete from 1, 2, or 3 to 6, 8, or 10 repetitions.

The footfall data of the companion animal is analyzed to convert the footfall data to the movement data listed above. The analysis of the footfall data includes any mathematical manipulation necessary to convert the footfall data per foot, per limb, or per motion into the desired piece of movement data. The movement data of the companion animal is inserted into a biological age equation developed from an analysis of the footfall data and movement data of a representative class of animals. The representative class of animals may have multiple biological equations which have been categorized according to chronological age. The biological equation utilized in the determination of the biological age of the companion animal is selected using the chronological age of the companion animal. Thus, the chronological age of the companion animal is utilized to determine which biological age equation to utilize. The calculated answer is the biological age of the companion animal.

In an embodiment, the biological age of the companion animal can be compared to the chronological age of that companion animal. A comparison between the biological age and the chronological age may be an indication that the biological age of the companion animal is better than, worse than, or the same as the chronological age. A biological age that is worse than the chronological age may be an indication of a problem in the health and/or well-being of the companion animal. The comparison between the biological age and the chronological age may result in a management program recommendation to maintain, enhance, or improve the biological age of the companion animal. A management program maintains the biological age of a companion animal when a subsequent determination of the biological age of the companion animal is consistent with the prior determination of the biological age. A management program enhances the biological age of a companion animal when a subsequent determination of the biological age of the companion animal indicates that a biological age which was already the same as or better than the chronological age is now better than the prior determination of the biological age. A management program improves the biological age of a companion animal when a subsequent determination of the biological age of the companion animal indicates that a biological age which was worse than the chronological age is now better than the prior determination of the biological age. The management program may include recommendations to maintain, enhance or improve the biological age of the companion animal according to the principles of sound veterinary medicine. Examples of recommendations the management program may include, but are not limited to, are dietary modification, supplement administration, weight loss/management plans, physical activity modifications, veterinary intervention, and combinations thereof. In an embodiment, the biological age of the companion animal is determined at a first moment in time. A subsequent determination of the biological age of the companion animal then occurs at a second later moment in time. The subsequent determination of the biological age of the companion animal is then compared to the biological age at the first moment in time. The subsequent determination of the biological age is an indication of an improvement, enhancement, deterioration, or maintenance of the first moment in time determination of the biological age of the companion animal. The comparison between the first moment in time determination and the subsequent determination allows for modification of the management program of the companion animal.

In an embodiment, the biological age of the companion animal is compared to a database comprising biological age information of a representative class of animals. A comparison of the biological age of the companion animal and the average biological age of the representative class of animals may be an indication that the biological age of the companion animal is better than, worse than, or is on par with the representative class of animals. An indication that the biological age of the companion animal is worse than the average biological age of the representative class of animals may be an indication of a problem in the health or well-being of the companion animal. The comparison of the biological age of the companion animal and the average biological age of the representative class of animals may result in a management program recommendation to maintain, improve or enhance the biological age of the companion animal. The management program may include recommendations to maintain, enhance or improve the biological age of the companion animal according to sound veterinary medicine. The management program may include, but is not limited to, dietary modification, supplement administration, weight loss/management plans, physical activity modifications, veterinary intervention, and combinations thereof. In an embodiment, the biological age of the companion animal is determined at a first moment in time. A subsequent determination of the biological age of the companion animal then occurs at a second later moment in time. The subsequent determination of the biological age of the companion animal is then compared to the biological age at the first moment in time. The subsequent determination of the biological age is an indication of an improvement, enhancement, deterioration, or maintenance of the first moment in time determination of the biological age of the companion animal. The comparison between the first moment in time determination and the subsequent determination allows for modification of the management program of the companion animal.

In the event that a management program is modified, the biological age of the companion animal may be determined again at another moment later in time. Following the later determination of the biological age of the companion animal a decision is made as to whether additional modifications to the management program are warranted. For example, in an embodiment, the management program includes a dietary modification. After the companion animal has followed the management program for a period of time the biological age of the companion animal is determined again and the management program is reviewed to decide if the diet should be modified again. In the event of a diet modification, the biological age of the companion animal can be determined again at later moment in time. In an embodiment, the management program includes feeding a supplement to a companion animal experiencing a physical ailment such as osteoarthritis. The supplement may be recommended as part of the management program to benefit the joints of the companion animal. Following the use of the supplement, the biological age of the companion animal is determined again. The later determination of the biological age allows for a decision as to the efficacy of the supplement in the improvement of the joints of the companion animal. Following the determination, the management program is reviewed for modifications.

A management program, such as discussed above, will take into consideration the chronological age of the companion animal, biological age of the companion animal as well as conformation data, medical history, and combinations thereof. Conformation data of the companion animal may be collected before, during, and/or after the companion animal ambulates across the pressure detection unit. The conformation data may be collected by utilizing a fabric/cloth measuring tape, a goniometer (such as for measurements of the hip and shoulder joint angles), a U-shaped caliper tool that can fit around the body of the companion animal and combinations thereof. FIG. 1 is an illustration of the skeletal formation of a companion animal 10 such as a dog. Conformation data includes, but is not limited to, length of the right and left front legs (measurements include from the proximal point of the scapular spine 12 to the Acromion process of the left/right scapula 14, from the Acromion process of the left/right scapula 14 to the left/right humeral epicondyle 16, from the left/right lateral humeral epicondyle 16 to the left/right ulnar styloid process 18, and from the left/right ulnar syloid process 18 to the distal condyle of left/right fifth metacarpal bone 20), length of left and right hind legs (measurements include from the crest of the wing of the ileum 22 to the left/right ischiatic tuberosity 24, from the left/right greater trochanter of femur 26 to the left/right lateran femoral epicondyle 28, from the left/right lateral femoral epicondyle 28 to the left/right lateral malleoulus of the tibia 30, and from the left/right lateral malleoulus of the tibia 30 to the distal condyle of the left/right fifth metatarsal bone 32), distance between the shoulders (measurements include from the Acromion process of the left scapula 14 to the Acromion process of the right scapula), distance between the hips (measurements include from the left greater trochanter of femur 26 to the right greater trochanter of femur), shoulder/hip joint angle measurements (measurements include the angle of the left/right scapula (from reference point 12 to reference point 14) versus the horizontal plane at the Acromium process of the left/right scapula 14, and the angle of the left/right ileum (from reference point 22 to reference point 24) versus the horizontal plane at the left/right greater trochanter of femur 26), length of the companion animal (measurements include from the proximal point of the scapular spine 12 to crest of the wing of the ileum 22, the measurements can also be divided into from the Acromium process of the left/right scapula 14 to the dorsal spinous process of the scapula 34 and the dorsal spinous process of the scapula 34 to crest of the wing of the ileum 22), height of the companion animal (measurements include from the bottom of the left/right front leg to proximal point of the scapular spine 12), neck length (measurements include from occipital protuberance on the back of the skull 36 to the manubrium 38), tail length (measurements include form the fused dorsal spinous process of sacrum caudal 40 to the coccygeal vertebra 42), and combinations thereof.

In an embodiment, a database contains information including, but not limited to, the chronological age, footfall data, movement data, conformation data, medical history, biological age, management program and combinations thereof of a companion animal. In an embodiment, each time the companion animal ambulates across a pressure detection unit, the resulting footfall data, movement data, biological age determination, and combinations thereof may be stored in the database. In an embodiment, the database is linked to a publicly accessible medium such as the internet. In such an embodiment, the breeder, owner or caregiver of the companion animal may access the database information regarding their companion animal.

In an embodiment, a personalized report containing the chronological age, footfall data, movement data, conformation data, medical history, biological age, management program and combinations thereof of a companion animal is provided to the owner, breeder or caregiver of the companion animal. The personalized report can be provided to the owner, breeder or caregiver following the ambulation of the companion animal across the pressure detection unit, following the determination of the biological age of the companion animal, or at a later moment in time such as through the mail or electronic mail, or may be obtainable from a publicly accessible medium and combinations thereof. The personalized report can detail the management program and recommendations for the health and well-being of the companion animal. In an embodiment, the personalized report provides summaries or detailed description of each repetition of the companion animal across the pressure detection unit and an overall assessment of the companion animal's health and well-being.

FIGS. 2-20 are illustrations of the construction of a pressure detection unit.

Figure 2:
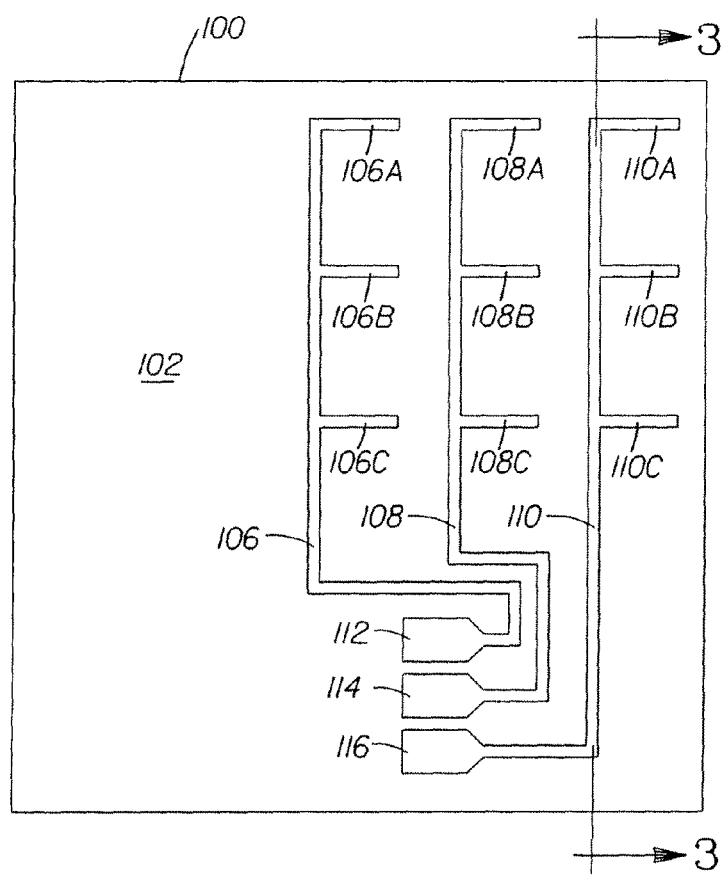
FIG. 2 is a top view of a portion of a first flexible material layer having traces of conductive material on an inner side to form the primary conductive traces.
Figure 3:
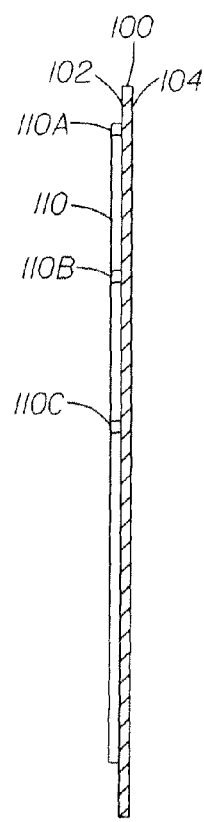
FIG. 3 is a cross section view along line 3-3 of the first flexible material layer of FIG. 2.

FIG. 2 illustrates a portion of a flexible material layer 100 for use in the collection of footfall data of a companion animal. FIG. 3 illustrates a cross section of the flexible material layer 100 of FIG. 2 viewed along line 3-3. Flexible material layer 100 has inner and outer sides, 102 and 104 respectively. The flexible material layer may be fabricated from materials such as Mylar® or Kapton®. Electrodes fabricated from a conductive material, such as silver or copper, are associated with the inner side 102 of the flexible material layer 100 to form primary conductive traces such as those indicated as 106, 108 and 110. Each primary conductive trace 106, 108 and 110 begins with a connecting primary finger 112, 114, and 116 and splits along the way to create multiple primary conductive sensor contact regions as indicated as regions 106A-C, 108A-C, and 110A-C on the end of primary conductive traces 106, 108, and 110 opposite connecting primary fingers 112, 114, and 116. It is understood that although the figures illustrate only three primary conductive traces 106, 108 and 110, the flexible material layer 100 may comprise numerous conductive traces as part of a much larger matrix. For simplification in explanation, more details follow with reference to electrode 110 which extends from connecting primary finger 116 as illustrated in FIG. 2. It is understood that the details with reference to electrode 110 are equally applicable to all other electrodes on the matrix.

Figure 4:
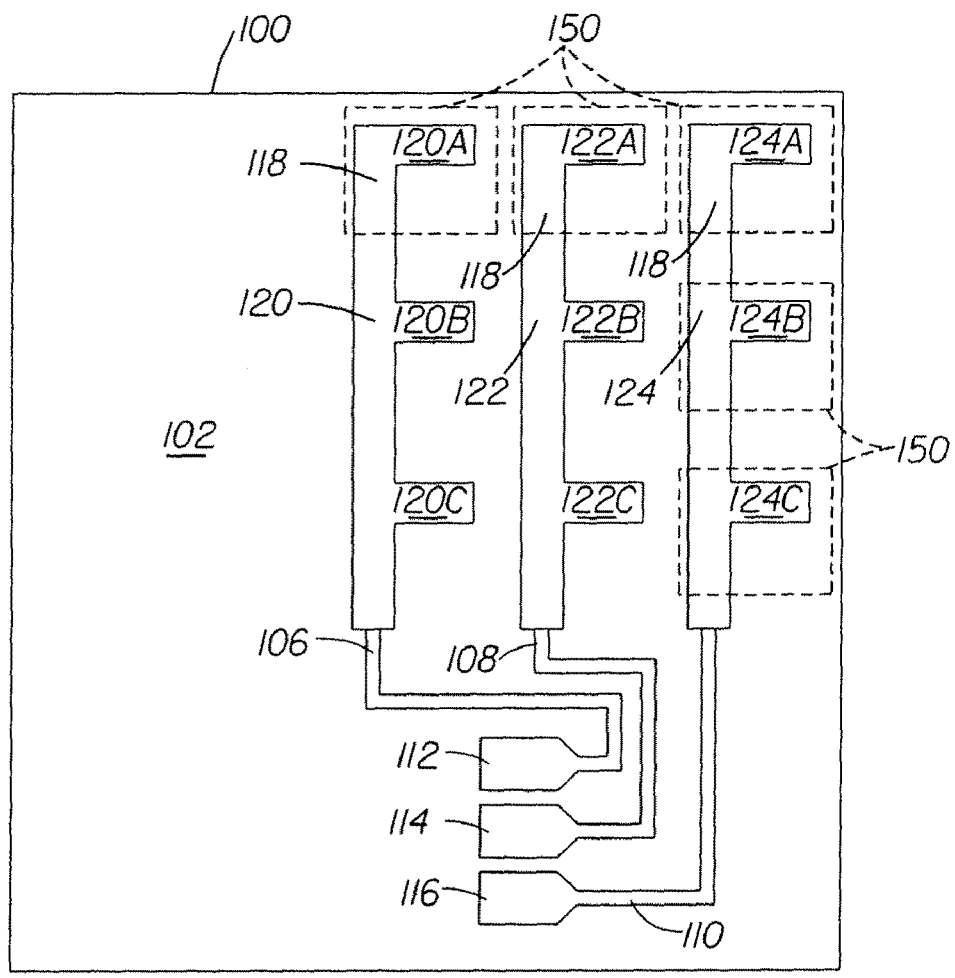
FIG. 4 is a top view of a portion of the first flexible material layer of FIG. 2 including a layer of pressure responsive resistive material which covers the primary conductive traces.

FIG. 4 illustrates the primary conductive sensor contact regions 110A, 110B, 110C (shown in FIG. 2) and a portion of the primary conductive trace 110 covered with a layer of pressure responsive resistive material 118 to form the primary resistive trace 124, and the corresponding primary resistive sensor contact regions 124A, 124B, and 124C. Each of the primary resistive sensor contact regions, 124A, 124B, and 124C, define multiple cells 150 arranged in a matrix over the area of flexible material layer 100. The pressure responsive resistive material may be any material such as described in U.S. Pat. No. 3,806,471, or other material such as material no. 4430 manufactured by Chomerics and material no. 4423S manufactured by Acheson Colloids.

Figure 5:
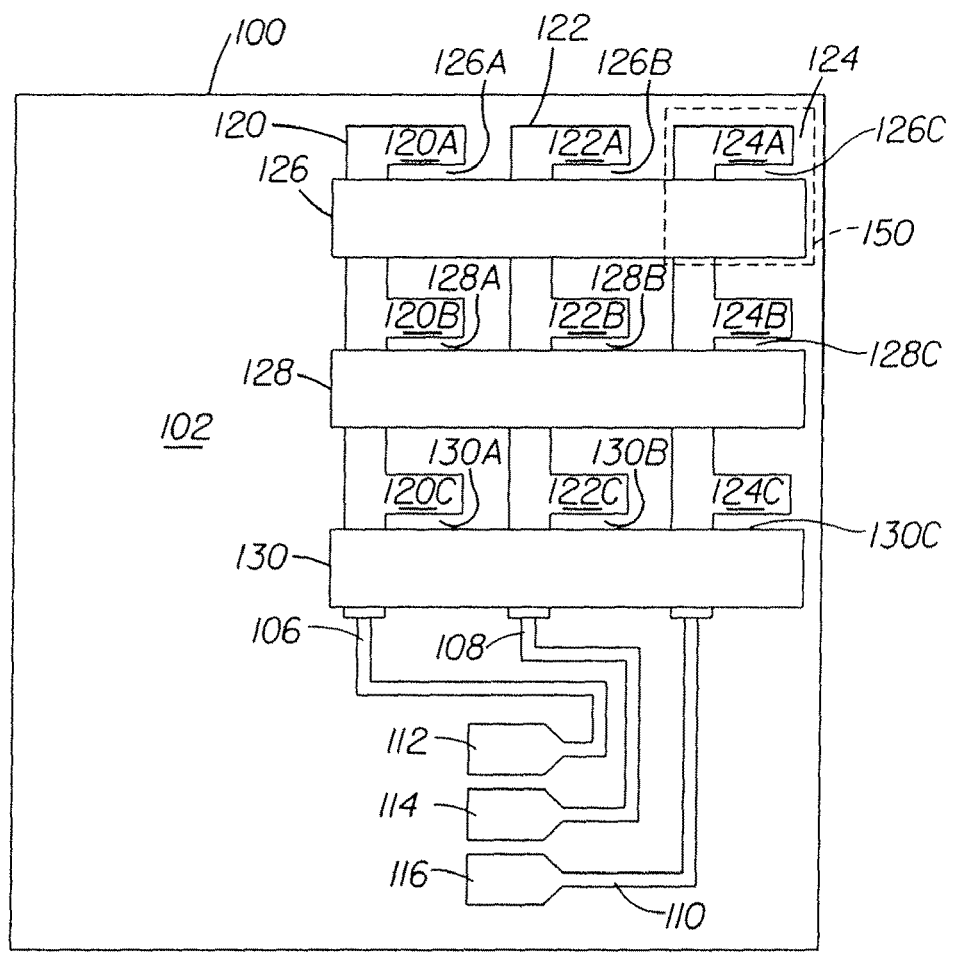
FIG. 5 is a top view of a portion of the first flexible material layer of FIG. 2 including strips of an insulating acrylic material at an angle crossing each primary resistive trace.

FIG. 5 is an illustration of traces of insulating material, such as material no. ML25198 manufactured by Acheson Colloids and indicated as 126, 128, and 130 which are silk-screened at an angle crossing primary resistive trace 124 (as well as the other primary resistive traces 120 and 122) and forming gaps, such as 126C, 128C, and 130C, between the primary resistive sensor contact regions 124A, 124B, and 124C of primary resistive trace 124 and the insulating traces 126, 128 and 130.

Figure 6:
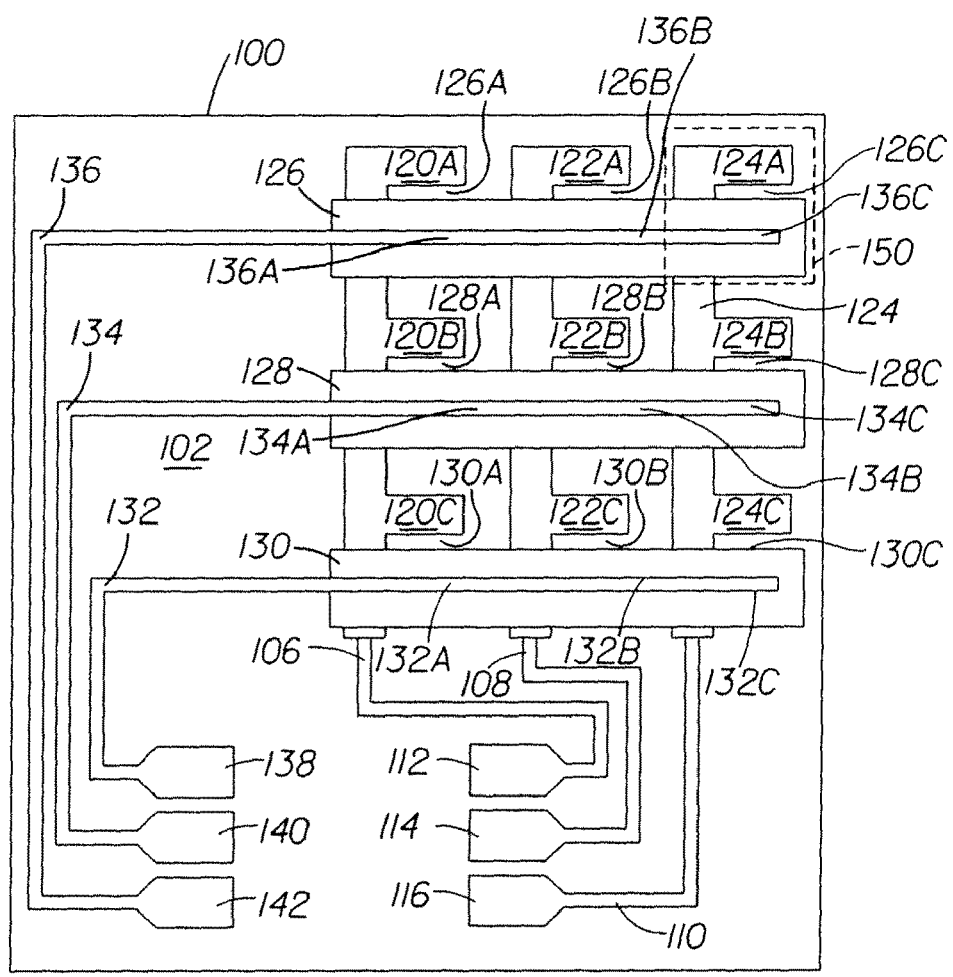
FIG. 6 is a top view of a portion of the first flexible material layer of FIG. 2 including secondary conductive traces on top of insulating acrylic material.

FIG. 6 illustrates secondary conductive traces 132, 134, and 136 which are silk-screened on top of the traces of insulating acrylic material such as 126, 128, and 130. The secondary conductive traces 132, 134 and 136 may be fabricated from strips of copper or silver similar to the primary conductive traces 106, 108 and 110. Each secondary conductive trace 132, 134, and 136 emanates from a connecting primary finger 138, 140, and 142 at one end, and which comprise a plurality of secondary conductive sensor contact regions 132A-C, 134A-C, and 136A-C on the opposite end. Connecting primary fingers 138, 140 and 142 are aligned opposite connecting primary fingers 112, 114, and 116 from which primary conductive traces 106, 108 and 110 emanate.

Figure 7:
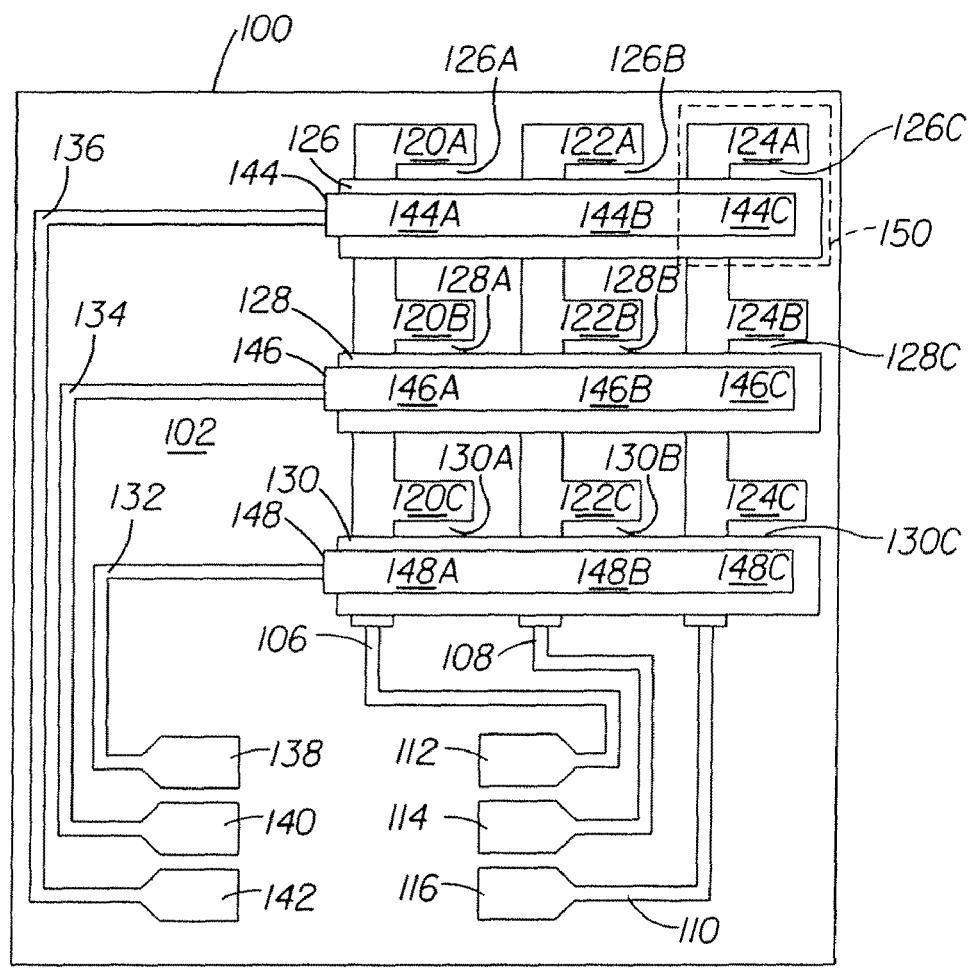
FIG. 7 is a top view of a portion of the first flexible material layer of FIG. 2 comprising secondary conductive traces which are covered lengthwise with a layer of pressure responsive resistive material to form secondary resistive traces.

FIG. 7 illustrates secondary conductive trace 132, 134, and 136 covered lengthwise with a layer of pressure responsive resistive material to form secondary resistive traces 148, 146, and 144. The layer of pressure responsive resistive material used to form the secondary resistive traces 144, 146, and 148 may be identical to the pressure responsive resistive material 118 (shown in FIG. 4) which is used to form primary resistive traces 120, 122, and 124. As illustrated, the layer of pressure responsive resistive material used to form the secondary resistive traces 144, 146, and 148 does not cover the width of each insulating acrylic material strip 126, 128 and 130. Also as illustrated, connecting primary fingers 138, 140, and 142 are not covered. Each secondary resistive trace 144, 146 and 148 defines a plurality of secondary resistive sensor contact regions such as indicated as 144C, 146C, and 148C. Secondary resistive sensor contact regions 144C, 146C, and 148C are separated from their corresponding primary resistive sensor contact regions 124A, 124B, and 124C.

Figure 8:
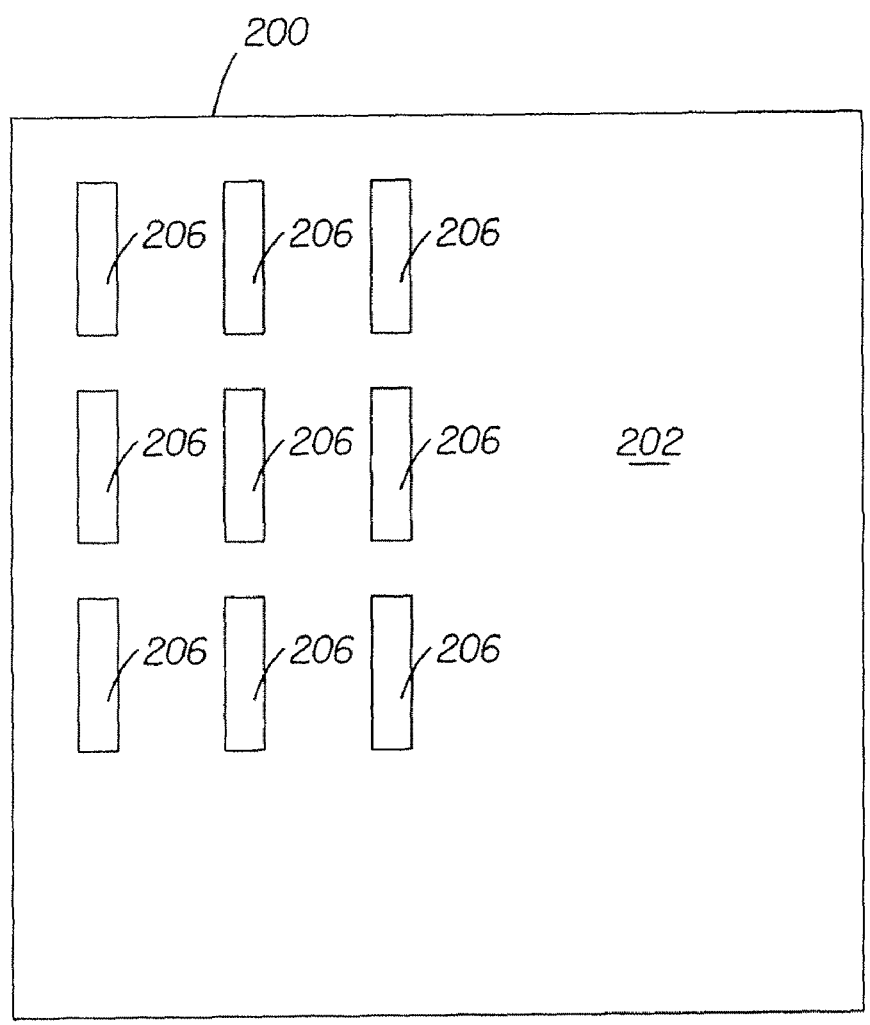
FIG. 8 is a top view of a second piece of flexible material with bridge conductive material traces or strips which are on the inner side of the second flexible material.

FIG. 8 illustrates a second piece of flexible material 200, such as Mylar® or Kapton®, having an inner side 202 with bridge conductive material traces 206 of silver or copper which are rectangular in shape and are silk-screened on inner side 202 of second flexible material 200. Bridge conductive material traces 206 are positioned on inner side 202 of second flexible material 200 in such a way that when inner surface 202 of second flexible material 200 securably overlays inner surface 102 (shown in FIG. 7) of first flexible material 100 (shown in FIG. 7), the bridge conductive material traces 206 will couple the primary resistive sensor contact regions 124A, 124B and 124C (shown in FIG. 7) to the secondary resistive sensor contact regions 144C, 146C, and 148C, (shown in FIG. 7) respectively.

Figure 9:
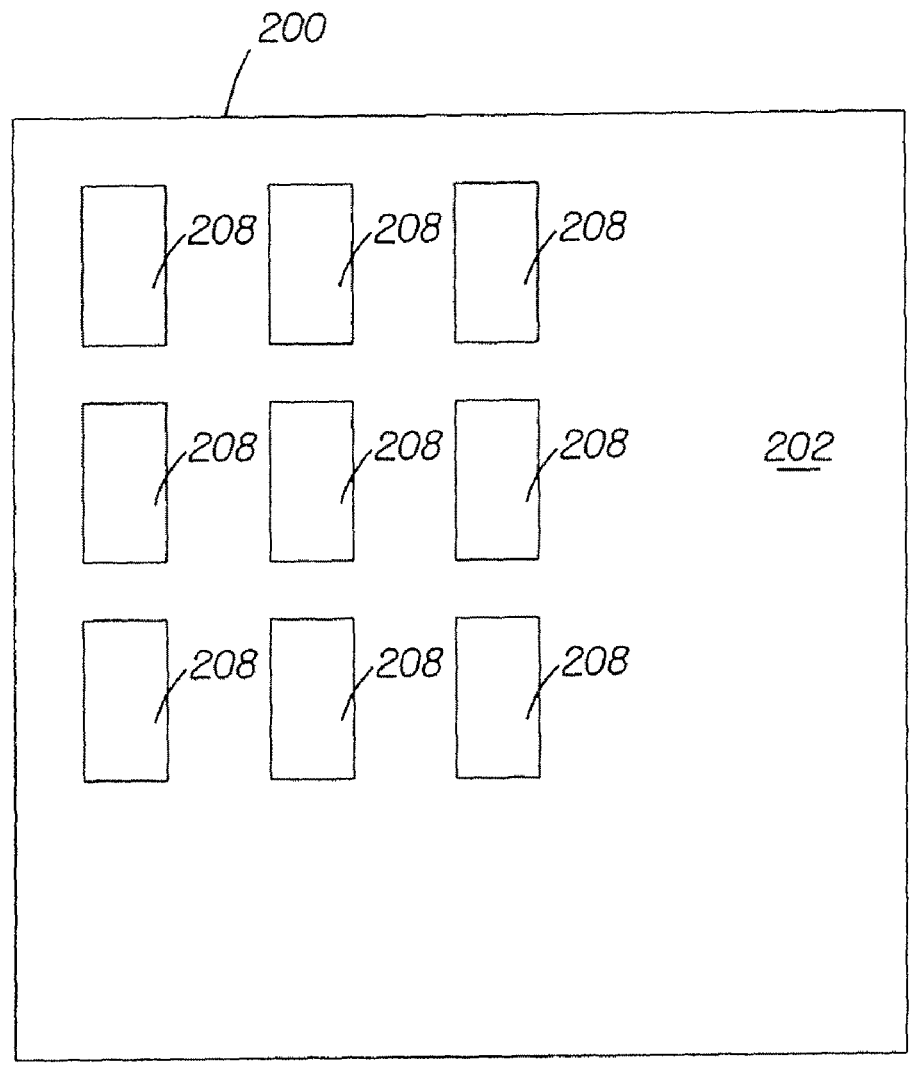
FIG. 9 is a top view of the bridge conductive material trace covered with a layer of pressure responsive resistive material to form bridge contact regions.

FIG. 9 illustrates that each bridge conductive material trace 206 (shown in FIG. 8) is covered with a layer of pressure responsive resistive material to form bridge contact regions 208. The pressure responsive resistive material may be the same material used to form the secondary resistive traces 144, 146, and 148 and the pressure responsive resistive material 118 used to form the primary resistive traces 120, 122, and 124 may have similar or different pressure/resistance properties.

Figure 10:
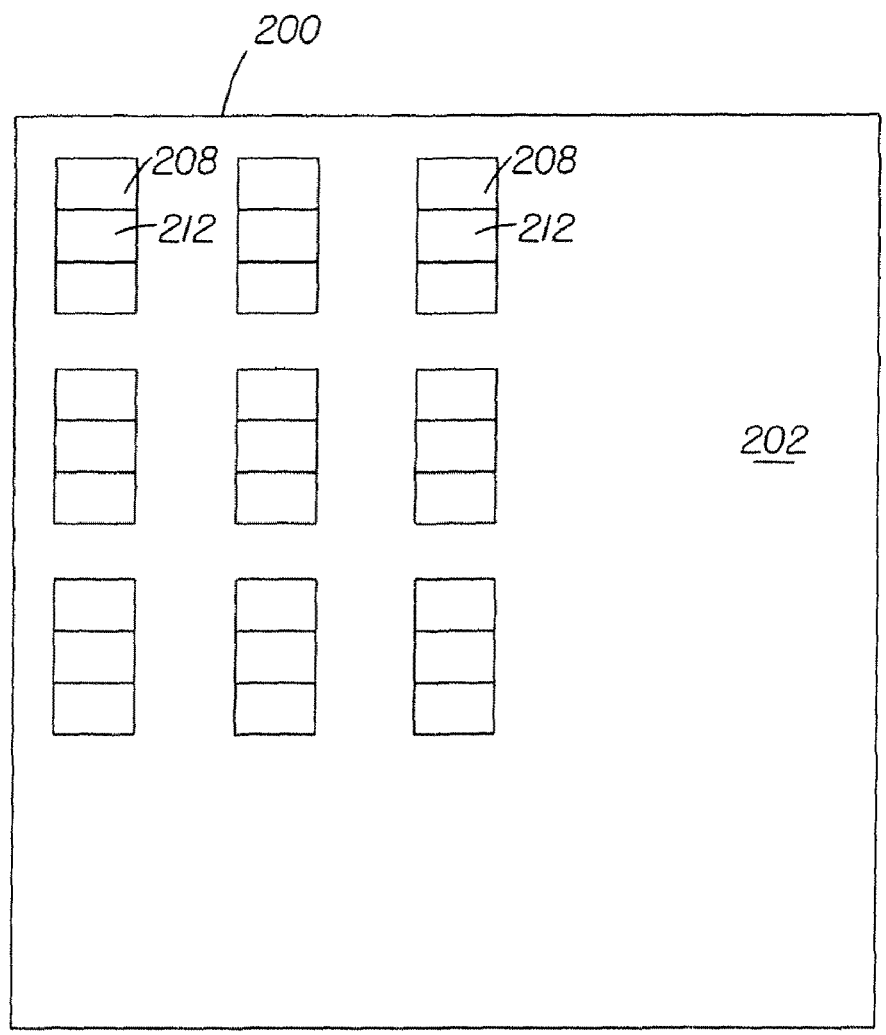
FIG. 10 is a top view of a rocker member across each bridge contact region after each bridge conductive material trace has been covered with pressure responsive resistive material to form the bridge contact region.

FIG. 10 illustrates a rocker member 212 which is silk-screened across each bridge contact region 208 after each bridge conductive material trace 206 (shown in FIG. 8) has been covered with pressure responsive resistive material to form the bridge contact region 208. The rocker member 212 is a piece of insulating material having a printable coating and may be ultra violet curable with flexible properties. The rocker member 212 is more rigid and less resilient than the surrounding material. For example, a rocker member 212 may be made of insulating material No. ML25198 manufactured by Acheson Colloids.

Figure 11:
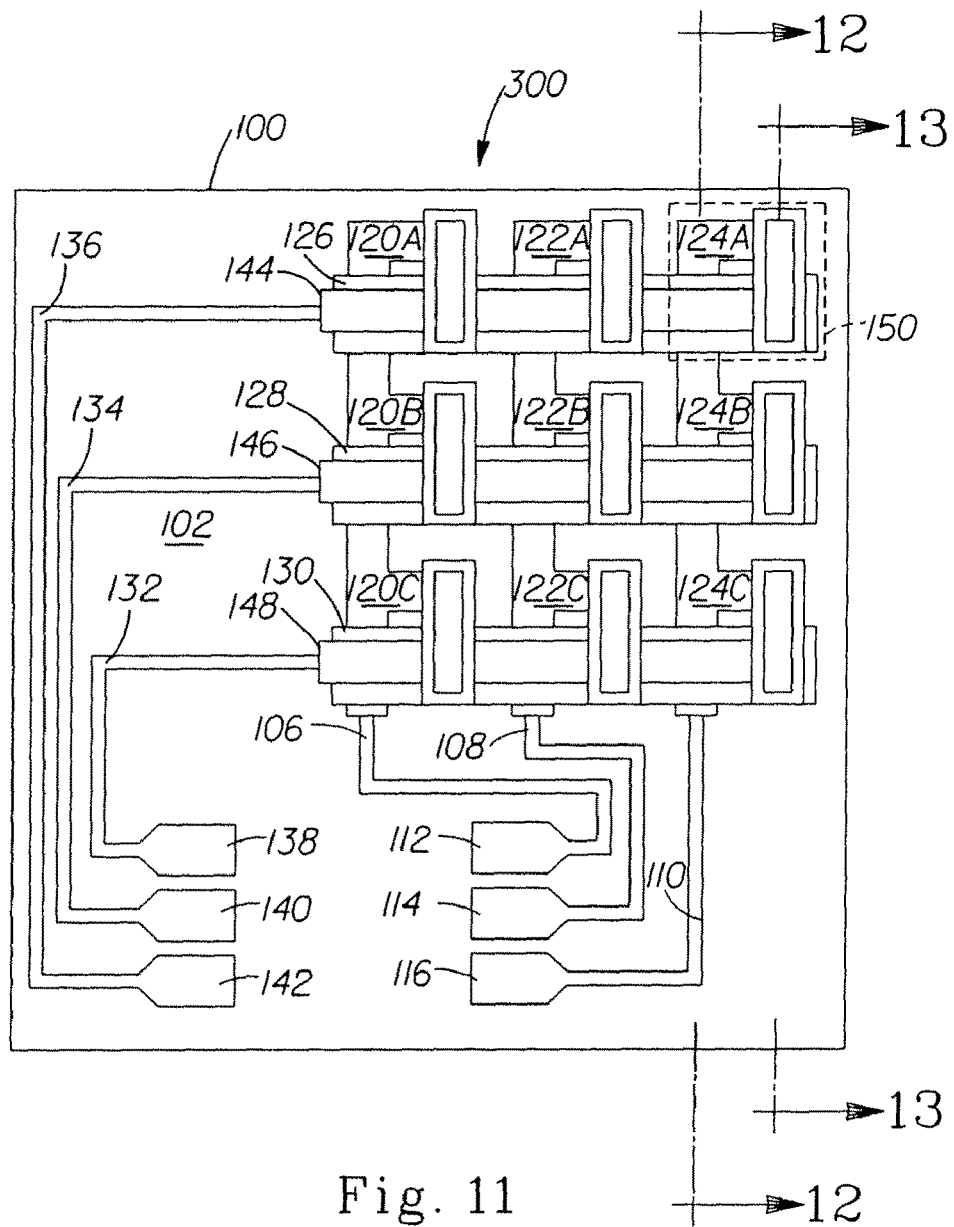
FIG. 11 a top view of a matrix comprising a plurality of conductive cells formed when the first flexible material and the second flexible material are overlaid upon each other.
Figure 12:
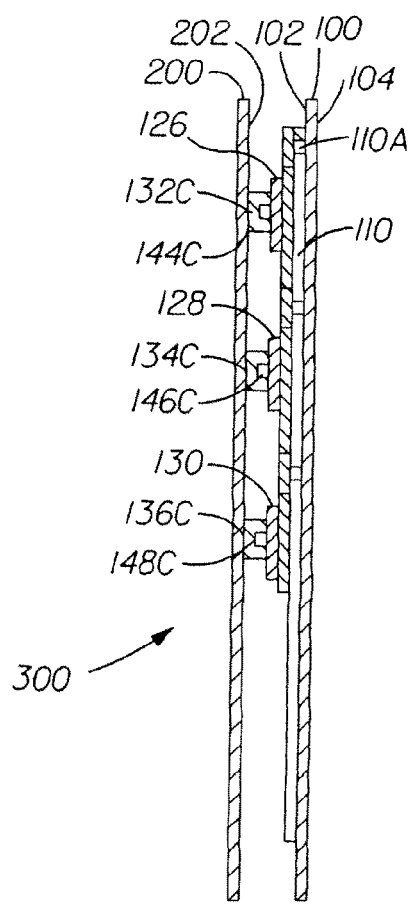
FIG. 12 is a cross-sectional view of the matrix of FIG. 11 viewed along line 12-12.
Figure 13:
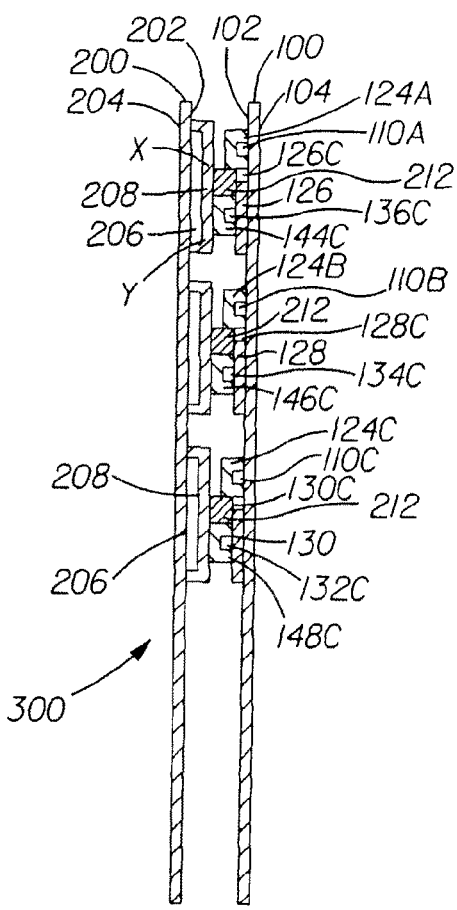
FIG. 13 is a cross-sectional view of the matrix of FIG. 11 viewed along line 13-13.

FIG. 11 illustrates the inner side 102 of first flexible material 100 and inner side 202 (shown in FIGS. 12 and 13) of second flexible material 200 (shown in FIGS. 12 and 13) brought together, overlaid upon each other and secured using an adhesive to define a matrix 300 comprising a plurality of conductive cells 150 defining a circuit. FIG. 12 illustrates a side view of the matrix 300 of FIG. 11 when viewed along line 12-12. FIG. 13 illustrates a side view of the matrix 300 of FIG. 11 when viewed along line 13-13. As illustrated in FIG. 13, when inner sides 102 and 202 are brought together and secured to one another, rocker members 212 are positioned so as to fit between the gaps such as indicated at 126C, 128C, and 130C. A load exerted on outer surface 104 of the first flexible material 100 over primary resistive sensor contact region 124A results in contact with one end of bridge contact region 208 on inner side 202 of second flexible material 200 at the point indicated by X. When the load is sufficiently large, the resistance of primary resistive sensor contact region 124A and the resistance of portion X of bridge contact region 208 becomes sufficiently small such that an electrical conduction can be established between primary conductive sensor contact region 110A and bridge conductive material trace 206.

Similarly, a load exerted on secondary resistive sensor contact region 144C results in contact with bridge contact region 208 on inner side 202 of second flexible material 200 at the point indicated by Y. When the load is sufficiently large, the resistance of secondary resistive sensor contact region 144C and the resistance of portion Y of bridge contact region 208 becomes sufficiently small such that an electrical conduction can be established between secondary conductive sensor contact region 136C and bridge conductive material trace 206.

However, if one load acts simultaneously over primary and secondary sensor contact regions 110A, 136C, then an electrical conduction can be established between primary conductive sensor contact region 111A and secondary conductive sensor contact region 136C through bridge conductive material trace 206. The pressure resistive material on the surfaces of secondary resistive sensor contact region 144C and bridge contact region 208 exhibits a low resistance between the two surfaces upon contact proportional to the load exerted between the two surfaces. Likewise, the pressure resistive material on surfaces of primary resistive sensor contact region 124A and bridge contact region 208 exhibits a low resistance between the two surfaces upon contact proportional to the force exerted between the two surfaces. As such, the amount of current present in secondary conductive sensor contact region 136C is proportional to the exerted load. Bridge contact region 208 ensures that all four surfaces, i.e., the upper surfaces of primary resistive sensor contact region 124A, bridge contact region 208 at point X, bridge contact region 208 at point Y and secondary resistive sensor contact region 144C, must be in contact for current to flow from primary conductive trace 111A conductor to secondary conductive sensor contact region 136C. Furthermore, rocker member 212 causes the primary and secondary resistive sensor contact regions 124A and 144C to revert to their original non-conductive state as soon as the load is removed.

Figures 14, 15:
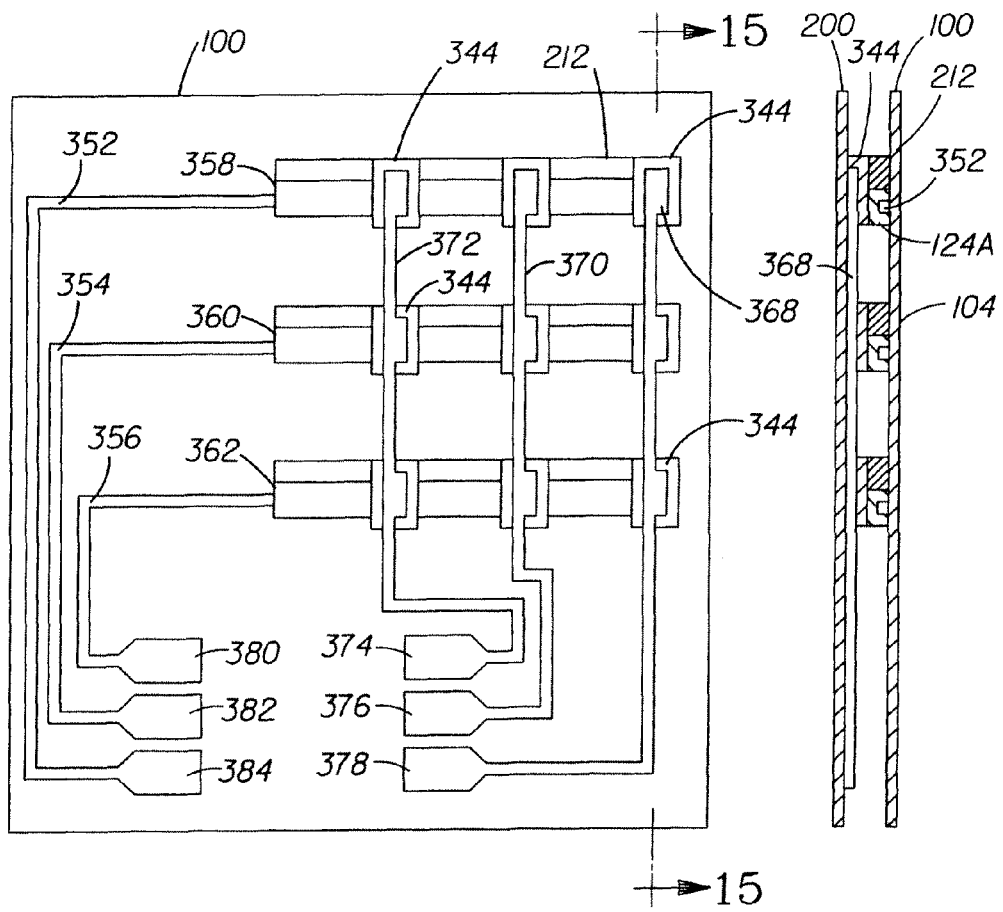
FIG. 14 is a top view of an alternative embodiment of a pressure detection unit.
FIG. 15 is a cross-sectional view of the matrix of FIG. 14 viewed along line 15-15.

FIG. 14 illustrates an alternative embodiment of the pressure detection unit. The pressure detection unit comprises first flexible backing material 100. Layers of primary conductive traces 352, 354, and 356 are disposed over flexible backing material 100 to form driving electrodes for conducting electric currents. Each primary conductive trace 352, 354, and 356 is longitudinally extended to form a driving electrode row that terminates with primary fingers 384, 382 and 380, respectively. Over a portion of each conductive trace 352, 354 and 356 a layer of pressure responsive resistive material is disposed to form primary resistive traces 358, 360 and 362, respectively.

A second flexible backing material 200 (shown in FIG. 15) is employed to receive layers of secondary conductive traces 368, 370 and 372 to form sensing electrodes for conducting electric currents. As shown in FIG. 14, each secondary conductive trace 368, 370 and 372 is longitudinally extended to form a sensing electrode column that terminates with a secondary finger such as 378, 376 and 374, respectively. Over a portion of each secondary conductive trace 368, 370 and 372, a layer of pressure responsive resistive material is disposed to form secondary resistive traces 344.

A rocker member 212 is disposed over each secondary resistive trace. Rocker member 212 is disposed in the form of a horizontal strip over secondary resistive traces 344, although that should not be considered limiting. For example, rocker member 212 may employ a width such that it only substantially covers each secondary resistive trace 344. Each rocker member 212 is made of a material that is more rigid than the pressure responsive resistive materials employed to form the arrangement.

Each primary conductive trace 352, 354 and 356 in combination with a corresponding secondary conductive trace 368, 370 and 372 and intermediate primary resistive traces 358, 360 and 362 and secondary resistive trace 344 along with rocker element 212, form a primary resistive sensor contact region such as 124A (shown in FIG. 15). For example, a primary resistive sensor contact region may be formed by a primary and secondary conductive trace separated by an intermediate pressure responsive resistive material and a rocker member that is extended within the gap defined by the primary and secondary conductive traces and the intermediate pressure responsive resistive material.

The two layers 100 and 200 are securably disposed over each other by an adhesive to form the arrangement illustrated in FIG. 15. During operation, when flexible layers 100 and 200 are not exposed to a load, each primary resistive sensor contact region exhibits a substantially high resistance or impedance due to the use of pressure responsive resistive materials that form primary and secondary resistive traces. When a load is exerted on either or both flexible backing layers 100 and 200, the resistance of each pressure responsive resistive material decreases until such time that a conductive contact is established between a driving and sensing electrode at the region where the load has been exerted. When the load is removed, rocker element 212 causes the pressure responsive resistive material to quickly revert back to their original state prior to the exertion of the load.

Rocker member 212 is made of a material that is more rigid than the pressure responsive resistive material and the time that it takes to revert to the original state is shorter than conventional sensors. When the load is removed the rocker member helps the primary resistive traces to revert back to their original state more rapidly. As the primary resistive traces revert back to their original state quicker than conventional sensors, it is possible to employ thicker flexible backing materials. The use of such backing materials will allow the user of the pressure detection unit to fold the backing material for easier transportation, without deformation of the pressure detection unit after repeated folding and unfolding.

Figure 16:
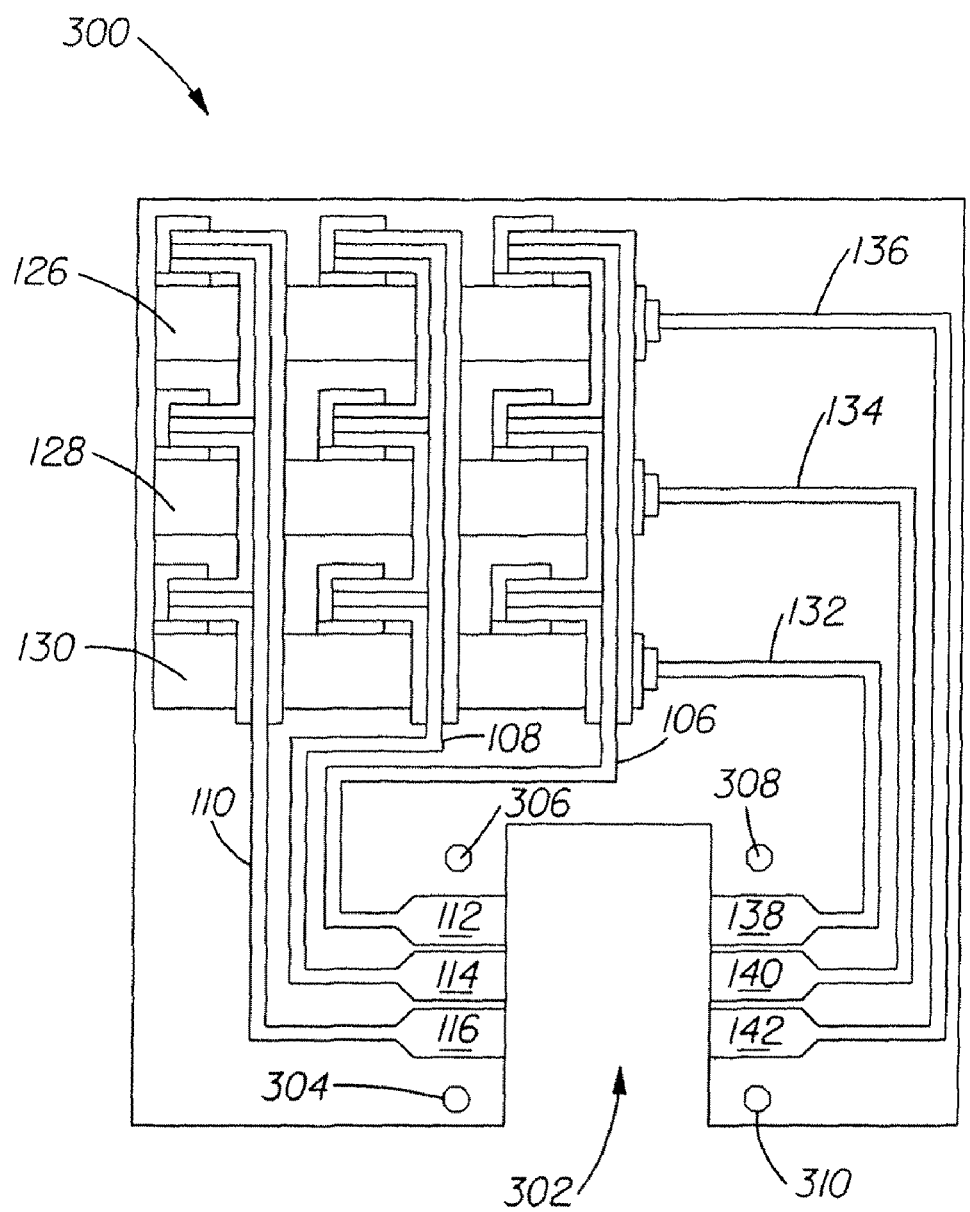
FIG. 16 is a top view of the matrix of FIG. 11 having a portion of the matrix cut away.

After inner sides 102 and 202 (shown in FIGS. 12 and 13) of the first and second flexible materials 100 and 200 (shown in FIGS. 12 and 13), respectively, are brought together and secured to define matrix 300, a portion of the combined flexible material layers is cut away, as indicated at 302, in the region of the matrix 300 between connecting primary fingers 112, 114, 116, and 138, 140, and 142, as illustrated in FIG. 16. Additionally, mounting holes 304, 306, 308 and 310 are punched about the boundary of cutout portion indicated at 302 for receiving screws 402 (shown in FIG. 18).

Figure 17:
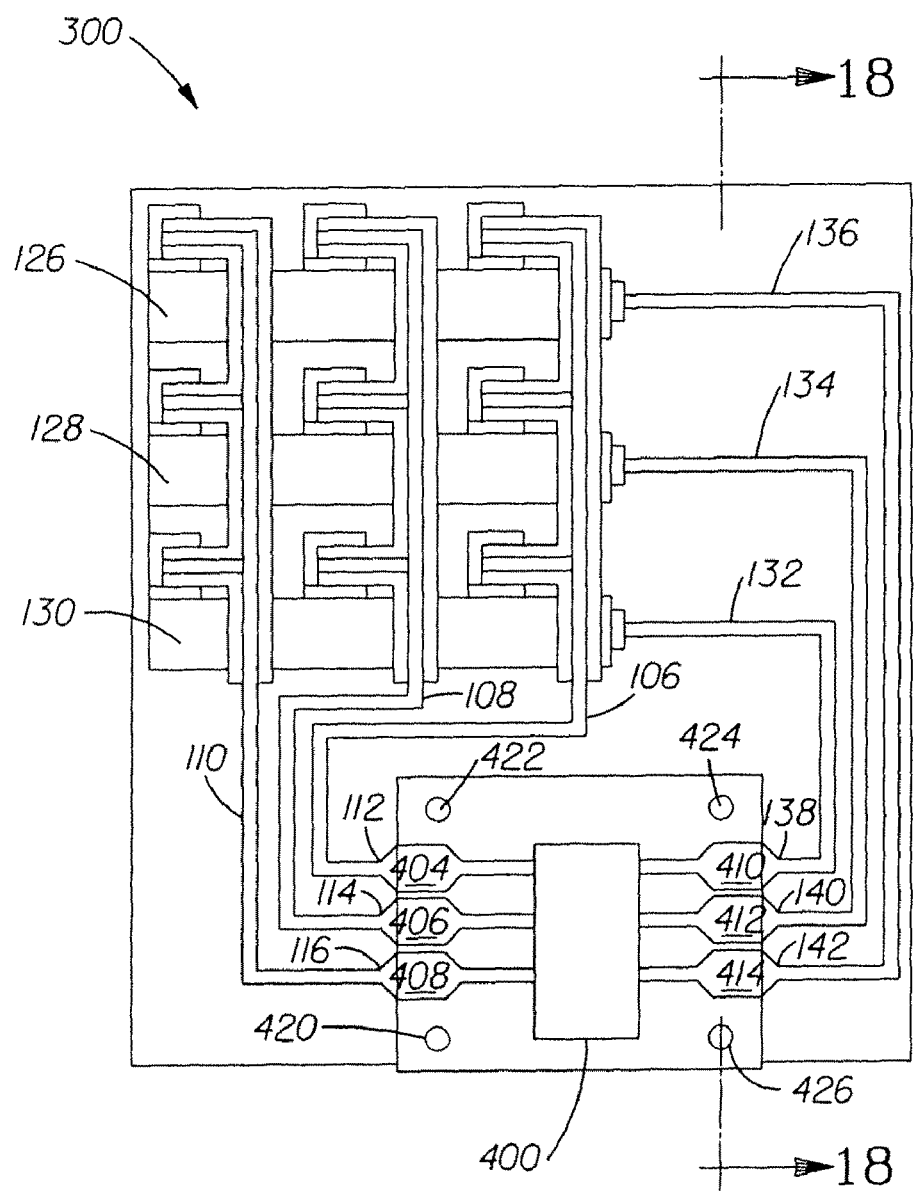
FIG. 17 is a top view of a circuit board containing the electronics having attached conductive fingers.
Figure 18:
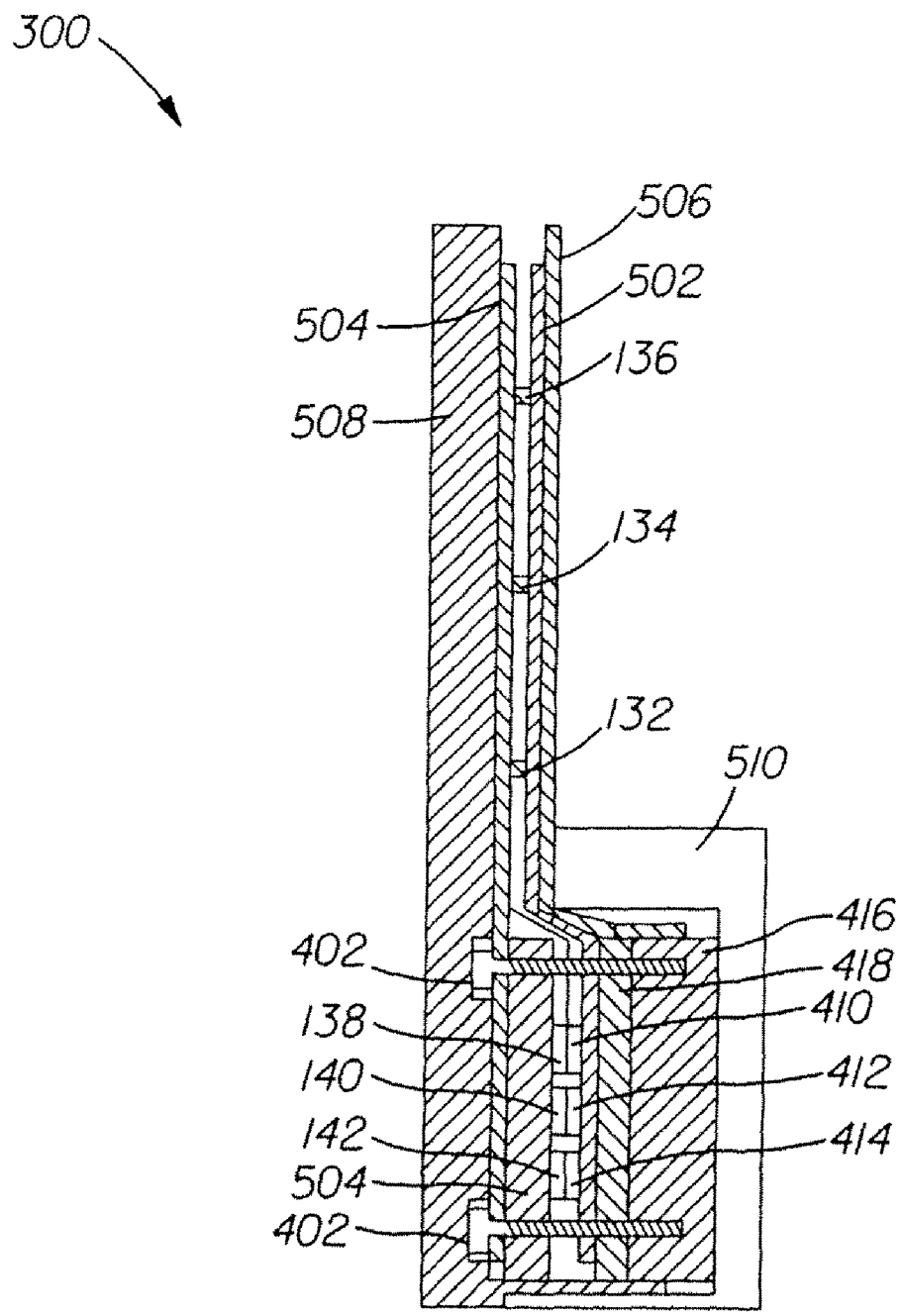
FIG. 18 is a cross-sectional view of the matrix of FIG. 17 viewed along line 18-18.

FIG. 17 is an illustration of a circuit board 400 containing the electronics having attached conductive fingers 404, 406, 408, 410, 412, and 414. Circuit board 400 generally includes a power source signal (not shown) for providing a current flow through matrix 300. A plurality of sensors (not shown) may be positioned on circuit board 400 opposite the electrical source such that the sensors detect a signal provided when the circuits on matrix 300 have been closed as a result of a force exerted on outer side 104 of first flexible material 100 (shown in FIGS. 12 and 13). Circuit board 400 is positioned such that connecting fingers 404, 406, 408 on one side of circuit board 400 are aligned with connecting primary fingers 112, 114, and 116 on matrix 300, and connecting fingers 410, 412, and 414 on the opposite side of circuit board 400 are aligned with connecting primary fingers 138, 140, and 142 on matrix 300. Circuit board 400 is further provided with mounting holes 420, 422, 424, and 426 which correspond with mounting holes 304, 306, 308, and 310 (shown in FIG. 16) in matrix 300 (shown in FIG. 16) for receiving screws therein. A gasket 416 (shown in FIG. 18) is then placed upon the periphery of the upper surface of circuit board 400 and a metal bar 418 is then disposed upon gasket 416 to receive screws 402 to facilitate securement of circuit board 400 with matrix 300.

The attachment of circuit board 400 and its electronics to matrix 300 comprises pressure detection unit 500 (shown in FIG. 19) having top surface 502 and a bottom surface 504 for recording the footfall data of a companion animal. Pressure detection unit 500 is comprised of numerous matrices 300A, 300B, and 300C comprised of numerous cells 150 (shown in FIG. 19). Pressure detection unit 500 is provided with a self adhesive open cell rubber material cover 508 (shown in FIG. 18) applied on bottom surface 504. The open cell rubber material 508 allows rocker member 212 to be depressed into the rubber so as to make contact with bottom surface 504 so that a current is generated. Open cell rubber material cover 508 also aids in protecting pressure detection unit 500 when it is rolled for storage or transport. Vinyl flexible material 506 (shown in FIG. 18) applied on top surface 502 also protects pressure detection unit 500 and permits easy cleaning and disinfection of pressure detection unit 500 after use. A cover 510 is placed over the electronics of circuit board 400 of each matrix 300.

Figure 19:
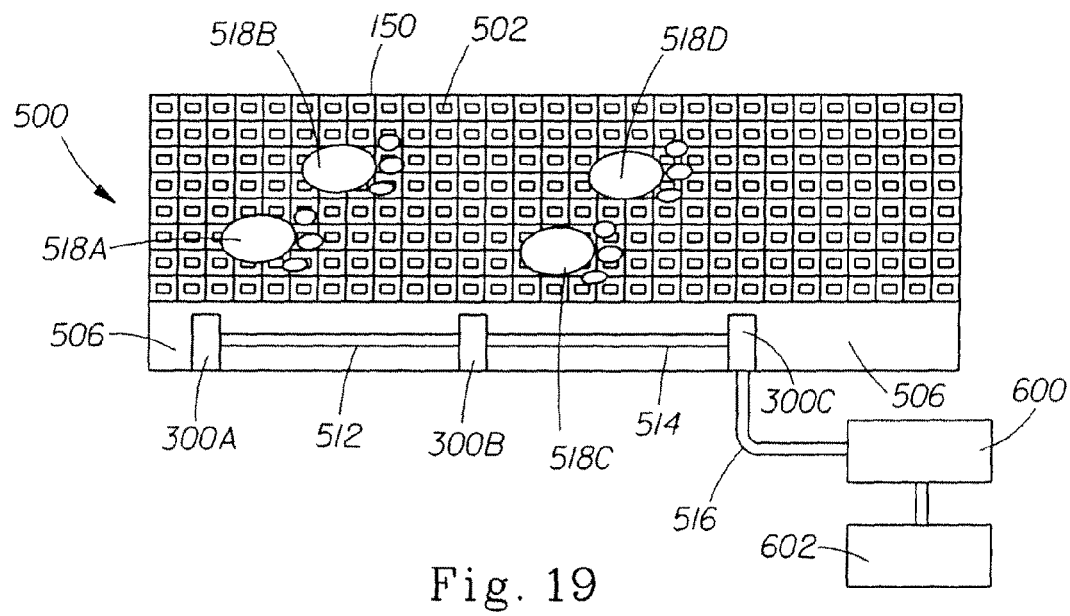
FIG. 19 is a top view of a pressure detection unit comprised of multiple matrices.

As shown in FIG. 19, a cable 512 connects the electronics of the matrix 300A to the electronics of the matrix 300B. A second cable 514 connects the electronics of matrix 300B to the matrix 300C and so on. It is understood that a single cable may be used to connect the matrices rather than a single cable connected between consecutive matrices. A third cable 516 connects the electronics of matrix 300C to a computer or microprocessor 600 having a video monitor 602 and which is loaded with a software program utilized for reading, recording, and analyzing the gait of a companion animal.

Figure 20:
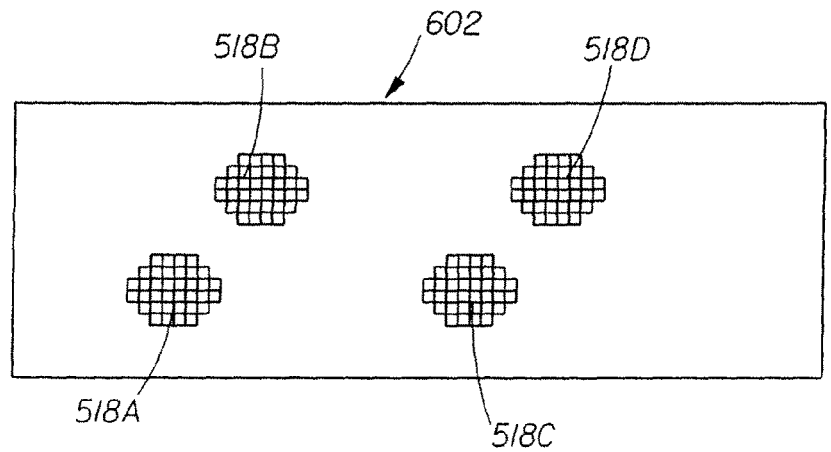
FIG. 20 is an illustration of a diagrammatic view of a companion animal's footprints upon the pressure detection unit of FIG. 19 as the footprints would appear on a video monitor.

In use, pressure detection unit 500 is laid upon a surface and the computer 600 is activated. Once it is ascertained that computer 600 is running properly and that first, second and third cables 512, 514, and 516 are tightly connected, a companion animal ambulates across pressure detection unit 500. The placement of the companion animal's feet 518A, 518B, 518C and 518D exert pressure upon the matrices 300A, 300B, 300C, such that circuits are closed wherein a current is caused to flow from a primary conductive trace, such as 110 in FIG. 11, across the resistive materials of the primary resistive sensor contacts, e.g. 124A, on first flexible material layer 100 and being received at a primary conductive sensor contact such as 136C. The flow of current in matrices 300A, 300B and 300C is converted to an electronic signal and communicated to personal computer 600 via first, second and third cables, 512, 514, and 516. Software loaded within computer 600 stores and displays the companion animal's footfall positions 518A, 518B, 518C, and 518D. FIG. 20 illustrates a representation of the footfalls of the companion animal 518A, 518B, 518C, and 518D ambulating upon pressure detection unit 500 as they might appear on video monitor 602 (shown in FIG. 19). The software loaded in computer 600 is then capable of reading, recording, and analyzing, according to one or more predetermined parameters, the footfalls of the companion animal. Additional details regarding the pressure detection unit may be found in U.S. Pat. No. 5,952,585 issued to Trantzas et al. on Sep. 14, 1999. An example of a pressure detection unit is a pressure detection unit and associated software as obtained from CIR Systems, Inc. (Havertown, Pa., Item # GRP-14Q).

The pressure detection unit 500 illustrated in FIGS. 19 and 20 is illustrated in the shape of a rectangular walkway. The pressure detection unit may comprise a shape selected from the group including, but not limited to, rectangle, square, circle, oval, trapezoid, and triangle. The pressure detection unit may comprise a size appropriate for the location and environment in which it will be placed and may be sized appropriately for the size of the companion animal that will ambulate upon the pressure detection unit. For example, collection of the footfall data of a cat may utilize a pressure detection unit that is smaller than the size of a pressure detection unit utilized in the collection of footfall data of a large dog.

EXAMPLE 1

Method for Collecting Footfall Data of a Representative Class of Animals

Two pressure detection units and associated software (the pressure detection units and associated software are as purchased from CIR Systems, Inc. (Havertown, Pa., Item # GRP-14Q)) are utilized to collect the footfall data of 120 Labrador Retrievers with no known physical ailments. The pressure detection units are in the shape of a rectangular walkway and are arranged end to end. The pressure detection units are associated with a computer via USB cables. In such an arrangement, each pressure detection unit operates independent of the other pressure detection unit.

With the assistance of an animal handler, each of the 120 Labrador Retrievers is guided at the pace of a trot for the completion of two gait cycles from a first region to a second region of the first pressure detection unit and immediately from a first region to a second region of the second pressure detection unit as the two units are placed end to end. The Labrador Retrievers range in age from 1.5 to 11 years of age and are distributed as follows: under 4 years of age: 24 animals, 4-8 years of age: 50 animals, over 8 years of age: 46 animals. The Labrador Retrievers are of typical body size and present with no known physical ailments. As each Labrador Retriever ambulates across the pressure detection units, the footfall placement of the Labrador Retriever is observed on the video monitor of the associated computer. Observing the footfalls on the video monitor provides a visual evaluation of whether the companion animal stays on the pressure detection units, whether all footfalls are captured by the pressure detection units, and whether the companion animal completes the desired number of gait cycles over the pressure detection units. In the event that the companion animal strays from the pressure detection units, not all footfalls are captured or the gait cycles are not completed, the movement is repeated. The footfall data of each Labrador Retriever is collected and stored on the associated computer.

EXAMPLE 2

Method of Analyzing the Footfall Data of Example 1 to Convert the Footfall Data to Movement Data and Develop Biological Age Equations The footfall data of Example 1 is analyzed to convert the footfall data into movement data of each Labrador Retriever. The analysis of the footfall data includes the mathematical manipulation necessary to convert the footfall data per foot, per limb or per motion into the desired piece of movement data—number of pressure sensors activated in a given paw placement, pressure peak (maximum amount of pressure in the series of steps of all four feet), pressure mean (average pressure of the four limbs), pressure time (the time, in seconds, of contact minus the stance time), step length (the distance, in centimeters, between the paw contact of one side of the body and the paw contact of the contra lateral side), stride length (distance, in centimeters, from the farthest hind point of paw to same point of next step), step time (time, in seconds, to complete the distance between the paw contact of one side of the body and the paw contact of the contra lateral side), stride time (time, in seconds, elapsed between the paw going down and the pawing going up), swing time (time, in seconds, elapsed between the paw going up and the paw going down), stance time (the time, in seconds, the paw is on the ground in seconds), distance (total distance covered measured in centimeters), ambulation time (total time, in seconds, the companion animal is on the pressure detection unit from the first step to the last pressure contact), velocity (distance covered in the ambulation divided by time, in centimeters per second), step count (number of steps taken), cadence (pattern of steps taken), step time of all four paws (the time, in seconds, to complete the distance between the paw contact of one side of the body and the paw contact of the contra lateral side (either front or hind)), step length measured individually on each leg (distance, in centimeters, between the contact of the front or hind leg and the contact of its contra lateral leg measured in centimeters), cycle time measured individually for each leg (the time, in seconds, elapsed for swing and stance phase combined), stride length measured individually for each leg (length of step, in centimeters, from toe off to contact for an individual leg), stride velocity measured individually on each leg (stride length covered in a cycle time, centimeters per second), swing percentage of cycle measured individually for each leg (percentage of time an individual limb is in motion and not in stationary phase), swing time measured individually for each leg (time, in seconds, limb is in air or swinging (from toe off to contact)), stance percentage of cycle measured individually for each leg (percentage of time limb is stationary in the cycle relative to the swing phase (contact toe off)), stance time, in seconds, measured individually for each leg, number of sensors measured individually for each leg (number of sensors for an individual leg), peak pressure measured individually for each leg, mean pressure measured individually for each leg, center of gravity (line of movement from the center of gravity of the subject.

To develop the biological age equations, all of the pieces of movement data are statistically analyzed by the Principal Component Method. The Principal Component Method utilizes all pieces of movement data to create a covariance matrix and to determine the eigenvectors. An 80% threshold is used throughout the Principal Component Method. The principal components are the linear combinations of the movement data and the interpretation of the principal components relies on the weight (the direction and magnitude) of the movement data. All pieces of movement data are mean-centered and scaled by standard deviation. A stepwise discriminate analysis is used to select a subset of principle components that are statistically significant in discriminating chronological age groups (p-value <0.05). The selected subsets of principle components are used in a regression model (linear regression and age regression) to develop biological age equations. As different chronological age groups correlate with different subsets of principal components, biological age equations are developed for each subset of principal components. The chronological age groups are categorized into the following chronological age categories: <4 years old, 5-6 years old, 7-9 years old, and >10 years old. Biological age equations developed based on the footfall data collected in Example 1 and categorized by chronological age group are as follows:

<4 years old:

Biological age=3.55-0.27*[ambulation time*-0.2954+cadence*0.2145+cycle time left front leg*-0.0551+cycle time left hind leg*-0.0450+cycle time right front leg*-0.0666+cycle time right hind leg*-0.0570+mean pressure as normalized by body weight of the left hind leg*-0.0580+mean pressure as normalized by body weight of left front leg*-0.1206+mean pressure as normalized by body weight of the right hind leg*-0.0513+mean pressure as normalized by body weight of the right front leg*-0.1117+peak pressure as normalized by body weight of the left hind leg*0.0536+peak pressure as normalized by body weight of the left front leg*-0.0556+peak pressure as normalized by body weight of the right hind leg*0.0604+peak pressure as normalized by body weight of the right front leg*-0.0412+stance per left front leg*-0.0645+stance per left hind leg*0.1822+stance per right front leg*-0.0880+stance per right hind leg*0.1738+stance time of left front leg*-0.0712+stance time of the left hind leg*0.1176+stance time of the right front leg*-0.0939+stance time of the right hind leg*0.1088+step count*-0.2591+stride length of the left front leg*0.2704+stride length of the left hind leg*0.2771+stride length of right front leg*0.2568+stride length of right hind leg*0.2662+stride velocity*0.3112+swing per left front leg*0.0654+swing per left hind leg*-0.1822+swing per right front leg*0.0877+swing per right hind leg*-0.1729+swing time of left front leg*0.0025+swing time of left hind leg*-0.1924+swing time right front leg*0.0089+swing time right hind leg*-0.1890+velocity*0.3103].

5-6 years old:
Biological age=5.5869+(−0.156)*[ambulation time*−0.0647+cadence*0.0324+cycle time left front leg*0.0768+cycle time left hind leg*0.0408+cycle time right front leg*0.0621+cycle time right hind leg*0.0475+mean pressure as normalized by body weight of left hind leg*0.3217+mean pressure as normalized by body weight of left front leg*−0.2509+mean pressure as normalized by body weight of right hind leg*0.2734+mean pressure as normalized by body weight of right front leg*−0.2109+peak pressure as normalized by body weight of left hind leg*0.4654+peak pressure as normalized by body weight of left front leg*−0.3876+peak pressure as normalized by body weight of right hind leg*0.3650+peak pressure as normalized by body weight of right front leg*−0.3341+stance per left front leg*−0.0086+stance per left hind leg*−0.0265+stance per right front leg*0.0565+stance per right hind leg*−0.1160+stance time left front leg*0.0476+stance time left hind leg*−0.0014+stance time right front leg*0.0757+stance time right hind leg*−0.0562+step count*−0.1084+stride length of left front leg*0.0127+stride length left hind leg*−0.0004+stride length right front leg*−0.0069+stride length right hind leg*−0.0192+stride velocity*−0.0551+swing per left front leg*0.0085+swing per left hind leg*0.0264+swing per right front leg*−0.0572+swing per right hind leg*0.0958+swing time left front leg*0.0744+swing time left hind leg*0.0538+swing time right front leg*0.0076+swing time right hind leg*0.1193+velocity*−0.0623]+(−0.203)*[ambulation time*−0.0164+cadence*−0.0959+cycle time left front leg*0.0709+cycle time left hind leg*−0.0525+cycle time right front leg*0.0561+cycle time right hind leg*−0.0213+mean pressure as normalized by body weight of left hind leg*0.2007+mean pressure as normalized by body weight of left front leg*0.0786+mean pressure as normalized by body weight of right hind leg*0.1914+mean pressure as normalized by body weight of right front leg*0.4709+peak pressure as normalized by body weight of left hind leg*−0.2582+peak pressure as normalized by body weight of left front leg*−0.4324+peak pressure as normalized by body weight of right hind leg*−0.2324+peak pressure as normalized by body weight of right front leg*0.0786+stance per left front leg*−0.2055+stance per left hind leg*0.1437+stance per right front leg*0.2088+stance per right hind leg*−0.0479+stance time left front leg*−0.0715+stance time left hind leg*0.0717+stance time right front leg*0.1433+stance time right hind leg*−0.0496+step count*−0.0750+stride length left front leg*0.0757+stride length left hind leg*0.0459+stride length right front leg*0.0482+stride length right hind leg*0.0213+stride velocity*0.0194+swing per left front leg*0.2059+swing per left hind leg*−0.1446+swing per right front leg*−0.2091+swing per right hind leg*0.0528+swing time left front leg*0.2413+swing time left hind leg*−0.1502+swing time right front leg*−0.0973+swing time right hind leg*0.0286+velocity*−0.0298]+(−0.05)*[ambulation time*0.0592+cadence*−0.1585+cycle time left front leg*0.2542+cycle time left hind leg*0.2619+cycle time right front leg*0.2524+cycle time right hind leg*0.2498+mean pressure as normalized by body weight of left hind leg*−0.1722+mean pressure as normalized by body weight of left front leg*−0.1515+mean pressure as normalized by body weight of right hind leg*−0.1699+mean pressure as normalized by body weight of right front leg*−0.1365+peak pressure as normalized by body weight of left hind leg*−0.0890+peak pressure as normalized by body weight of left front leg*−0.0275+peak pressure as normalized by body weight of right hind leg*−0.0644+peak pressure as normalized by body weight of right front leg*−0.0055+stance per left front leg*0.2111+stance per left hind leg*0.1307+stance per right front leg*0.1930+stance per right hind leg*0.1398+stance time left front leg*0.2773+stance time left hind leg*0.2318+stance time right front leg*0.2725+stance time right hind leg*0.2374+step count*−0.0683+stride length left front leg*0.0982+stride length left hind leg*0.1062+stride length right front leg*0.0927+stride length right hind leg*0.1116+stride velocity*−0.1406+swing per left front leg*−0.2107+swing per left hind leg*−0.1310+swing per right front leg*−0.1932+swing per right hind leg*−0.1339+swing time left front leg*0.0681+swing time left hind leg*0.0705+swing time right front leg*0.0822+swing time right hind leg*0.0391+velocity*−0.1353]+(−0.999)*[ambulation time*0.0533+cadence*0.1168+cycle time left front leg*−0.2425+cycle time left hind leg*−0.1704+cycle time right front leg*0.2521+cycle time right hind leg*0.0939+mean pressure as normalized by body weight of left hind leg*0.1837+mean pressure as normalized by body weight of left front leg*0.0067+mean pressure as normalized by body weight of right hind leg*−0.0520+mean pressure as normalized by body weight of right front leg*−0.1562+peak pressure as normalized by body weight of left hind leg*−0.1042+peak pressure as normalized by body weight of left front leg*0.0114+peak pressure as normalized by body weight of right hind leg*0.0092+peak pressure as normalized by body weight of right front leg*0.0740+stance per left front leg*−0.0468+stance per left hind leg*0.0173+stance per right front leg*0.0592+stance per right hind leg*−0.0754+stance time left front leg*−0.1538+stance time left hind leg*−0.1122+stance time right front leg*0.1644+stance time right hind leg*0.0770+step count*0.0974+stride length left front leg*0.1097+stride length left hind leg*0.5845+stride length right front leg*−0.3395+stride length right hind leg*−0.1485+stride velocity*0.0550+swing per left front leg*0.0560+swing per left hind leg*−0.0153+swing per right front leg*−0.0595+swing per right hind leg*−0.0243+swing time left front leg*−0.2231+swing time left hind leg*−0.0896+swing time right front leg*0.2348+swing time right hind leg*0.0297+velocity*−0.2002].

7-9 years old:
Biological age=8.023+0.2322*[ambulation time*0.0961+cadence*−0.1347+cycle time left front leg*0.0668+cycle time left hind leg*0.0675+cycle time right front leg*0.0919+cycle time right hind leg*0.0479+mean pressure as normalized by body weight left hind leg*0.2685+mean pressure as normalized by body weight left front leg*0.3199+mean pressure as normalized by body weight right hind leg*0.2956+mean pressure as normalized by body weight right front leg*0.3247+peak pressure as normalized by body weight left hind leg*0.2993+peak pressure as normalized by body weight left front leg*0.3658+peak pressure as normalized by body weight right hind leg*0.3543+peak pressure as normalized by body weight of right front leg*0.3498+stance per left front leg*0.0467+stance per left hind leg*0.0218+stance per right front leg*−0.0164+stance per right hind leg*0.0775+stance time left front leg*0.0697+stance time left hind leg*0.0620+stance time right front leg*0.0529+stance time right hind leg*0.0917+step count*0.0696+stride length left front leg*0.1291+stride length left hind leg*0.1102+stride length right front leg*0.1341+stride length right hind leg*0.0974+stride velocity*0.0354+ swing per left front leg*−0.0468+swing per left hind leg*−0.0215+swing per right front leg*0.0150+swing per right hind leg*−0.0877+swing time left front leg*0.0226+swing time left hind leg*0.0159+swing time right front leg*0.0938+swing time right hind leg*−0.0430+velocity*0.0340].

>10 years old:

Biological age=10.63−3.56*[ambulation time*0.0318+cadence*−0.1260+cycle time left front leg*0.0810+cycle time left hind leg*0.0119+cycle time right front leg*0.0242+cycle time right hind leg*−0.0783+mean pressure as normalized by body weight left hind leg*−0.0107+mean pressure as normalized by body weight left front leg*0.1204+mean pressure as normalized by body weight right hind leg*−0.0213+mean pressure as normalized by body weight right front leg*−0.0622+peak pressure as normalized by body weight left hind leg*0.0105+peak pressure as normalized by body weight left front leg*−0.0780+peak pressure as normalized by body weight right hind leg*0.0398+peak pressure as normalized by body weight right front leg*0.0417+stance per left front leg*0.0839+stance per left hind leg*0.0792+stance per right front leg*0.0500+stance per right hind leg*0.4486+stance time left front leg*−0.0229+stance time left hind leg*−0.0792+stance time right front leg*−0.0666+stance time right hind leg*−0.2061+step count*−0.1118+stride length left front leg*−0.4047+stride length left hind leg*0.2987+stride length right front leg*−0.1552+stride length right hind leg*−0.1422+stride velocity*−0.0558+swing per left front leg*−0.0932+swing per left hind leg*−0.0741+swing per right front leg*−0.0741+swing per right hind leg*0.1937+swing time left front leg*0.1790+swing time left hind leg*0.1084+swing time right front leg*0.1209+swing time right hind leg*0.1224+velocity*0.4765].

Example 3

Determination of Biological Age of Individual Labrador Retriever-Like Companion Animals To determine the biological age of an individual companion animal such as a Labrador Retriever or a Labrador Retriever-like companion animal, the movement data from that companion animal is inserted into the appropriate biological age equation developed from the movement data of a representative class of animals which has been categorized into a chronological age group corresponding to that companion animal's chronological age. Thus, the movement data of a Labrador Retriever or Labrador Retriever-like companion animal whose chronological age is under 4 years of age would be inserted into the biological age equation developed in Example 2 for <4 years old. The movement data of a Labrador Retriever or Labrador Retriever-like companion animal whose chronological age is 8 years of age would be inserted into the biological age equation developed in Example 2 for 7-9 years old. The biological age is the calculated age result following insertion of the movement data into the appropriate biological age equation. While the chronological age of the Labrador Retriever or Labrador Retriever-like companion animal is utilized to determine which biological age equation to utilize, the resultant biological age may be outside of that chronological age range.

The footfall data of two companion animals, such as two Labrador Retriever-like companion animals, is collected by following the method of Example 1. Both companion animals have a chronological age of three years of age and present with no known physical ailments. Companion Animal #1 has a weight of about 29 pounds. Companion Animal #2 has a weight of about 49 pounds. Each companion animal is guided through at least two gait cycles over the pressure detection units for three repetitions in the collection of footfall data. The footfall data is then analyzed using any mathematical manipulation necessary to convert the footfall data to movement data. The movement data from each repetition is as follows in Table 2:

TABLE 2

| Movement Data | Companion Animal #1 | | | Companion Animal #2 | | |
|---|---|---|---|---|---|---|
| | $1^{st}$ Repetition | $2^{nd}$ Repetition | $3^{rd}$ Repetition | $1^{st}$ Repetition | $2^{nd}$ Repetition | $3^{rd}$ Repetition |
| Distance (cm) | 218.44 | 225.43 | 346.71 | 273.69 | 307.98 | 319.41 |
| Ambulation Time (sec) | 69.60 | 68.40 | 108 | 82.80 | 82.20 | 81.60 |
| Velocity (cm/s) | 3.14 | 3.30 | 3.21 | 3.31 | 3.75 | 3.91 |
| Step Count | 12 | 12 | 16 | 16 | 16 | 16 |
| Cadence | 155.2 | 157.9 | 133.3 | 173.9 | 175.2 | 176.5 |
| Step Time (sec) Left Front | −0.005 | 0.008 | 0.011 | 0.049 | 0.068 | 0.068 |
| Step Time (sec) Right Front | 0.033 | 0.044 | 0.026 | 0.042 | 0.067 | 0.076 |
| Step Time (sec) Left Hind | −0.026 | −0.032 | 0.003 | 0.022 | 0.017 | 0.015 |
| Step Time (sec) Right Hind | −0.039 | −0.03 | −0.039 | 0.012 | 0.004 | 0.012 |
| Step Length (cm) Left Front | 115.325 | 118.75 | 118.184 | 94.594 | 102.9 | 110.198 |
| Step Length (cm) Right Front | 115.921 | 121.975 | 115.907 | 93.691 | 103.867 | 109.8 |
| Step Length (cm) Left Hind | 7.861 | 10.411 | 5.603 | 4.932 | 6.65 | 5.153 |

TABLE 2-continued

| Movement Data | Companion Animal #1 | | | Companion Animal #2 | | |
|---|---|---|---|---|---|---|
| | 1st Repetition | 2nd Repetition | 3rd Repetition | 1st Repetition | 2nd Repetition | 3rd Repetition |
| Step Length (cm) Right Hind | 9.981 | 8.118 | 7.112 | 4.467 | 5.412 | 4.955 |
| Cycle Time (sec) Left Front | 0.567 | 0.569 | 0.575 | 0.461 | 0.455 | 0.433 |
| Cycle Time (sec) Right Front | 0.579 | 0.542 | 0.599 | 0.46 | 0.445 | 0.454 |
| Cycle Time (sec) Left Hind | 0.567 | 0.542 | 0.57 | 0.442 | 0.443 | 0.442 |
| Cycle Time (sec) Right Hind | 0.556 | 0.559 | 0.553 | 0.454 | 0.447 | 0.447 |
| Stride Length (cm) Left Front | 107.348 | 112.777 | 117.716 | 92.793 | 102.722 | 104.408 |
| Stride Length (cm) Right Front | 109.311 | 114.039 | 115.612 | 91.512 | 101.15 | 106.882 |
| Stride Length (cm) Left Hind | 111.939 | 111.748 | 117.097 | 91.32 | 99.322 | 107.944 |
| Stride Length (cm) Right Hind | 106.457 | 114.993 | 112.099 | 91.231 | 99.77 | 106.268 |
| Swing Percentage of Cycle Left Front | 44.1 | 44.5 | 46.1 | 58.4 | 60.4 | 59.4 |
| Swing Percentage of Cycle Right Front | 49.7 | 51.8 | 46.6 | 53.7 | 60.4 | 60.6 |
| Swing Percentage of Cycle Left Hind | 49.6 | 51.5 | 54.4 | 56.6 | 58.7 | 58.6 |
| Swing Percentage of Cycle Right Hind | 49.1 | 50.8 | 50.3 | 54 | 56.6 | 55 |
| Swing Time (sec) Left Front | 0.25 | 0.253 | 0.265 | 0.269 | 0.275 | 0.257 |
| Swing Time (sec) Right Front | 0.288 | 0.281 | 0.279 | 0.247 | 0.269 | 0.275 |
| Swing Time (sec) Left Hind | 0.281 | 0.279 | 0.31 | 0.25 | 0.26 | 0.259 |
| Swing Time (sec) Right Hind | 0.273 | 0.284 | 0.278 | 0.245 | 0.253 | 0.246 |
| Stance Percentage of Cycle Left Front | 55.9 | 55.7 | 53.9 | 41.6 | 39.8 | 40.6 |
| Stance Percentage of Cycle Right Front | 50.4 | 48 | 53.3 | 46.3 | 39.3 | 39.4 |
| Stance Percentage of Cycle Left Hind | 50.3 | 48.5 | 45.6 | 43.4 | 41.3 | 41.4 |
| Stance Percentage of Cycle Right Hind | 50.9 | 49.2 | 49.7 | 46.3 | 43.4 | 45 |
| Stance Time (sec) Left Front | 0.317 | 0.317 | 0.31 | 0.192 | 0.181 | 0.176 |
| Stance Time (sec) Right Front | 0.292 | 0.26 | 0.319 | 0.213 | 0.175 | 0.179 |
| Stance Time (sec) Left Hind | 0.285 | 0.263 | 0.26 | 0.192 | 0.183 | 0.183 |
| Stance Time (sec) Right Hind | 0.283 | 0.275 | 0.275 | 0.21 | 0.194 | 0.201 |

TABLE 2-continued

| Movement Data | Companion Animal #1 | | | Companion Animal #2 | | |
|---|---|---|---|---|---|---|
| | $1^{st}$ Repetition | $2^{nd}$ Repetition | $3^{rd}$ Repetition | $1^{st}$ Repetition | $2^{nd}$ Repetition | $3^{rd}$ Repetition |
| Number of Sensors Left Front | 23.333 | 27.333 | 24.5 | 17 | 17.25 | 17.25 |
| Number of Sensors Right Front | 19 | 21.667 | 21 | 16 | 14.75 | 16.25 |
| Number of Sensors Left Hind | 20.667 | 21 | 20.25 | 15 | 16.75 | 15 |
| Number of Sensors Right Hind | 21.667 | 22.333 | 21.5 | 14 | 15 | 19.75 |
| Peak Pressure Left Front | 74.667 | 79.667 | 76.25 | 44.25 | 48.5 | 44.25 |
| Peak Pressure Right Front | 55.667 | 54.333 | 53.75 | 44.25 | 40.75 | 41.75 |
| Peak Pressure Left Hind | 56.667 | 60.333 | 52.75 | 34.5 | 40.25 | 35 |
| Peak Pressure Right Hind | 61.667 | 62.667 | 59 | 35.5 | 32.5 | 42.5 |
| Mean Pressure Left Front | 3.182 | 2.919 | 3.115 | 2.611 | 2.854 | 2.493 |
| Mean Pressure Right Front | 2.933 | 2.501 | 2.574 | 2.777 | 2.783 | 2.568 |
| Mean Pressure Left Hind | 2.74 | 2.873 | 2.615 | 2.344 | 2.449 | 2.416 |
| Mean Pressure Right Hind | 2.874 | 2.809 | 2.77 | 2.55 | 2.179 | 2.153 |
| Stride Velocity Left Front (cm/s) | 1.893 | 1.982 | 2.047 | 2.013 | 2.258 | 2.411 |
| Stride Velocity Right Front (cm/s) | 1.888 | 2.104 | 1.930 | 1.989 | 2.273 | 2.354 |
| Stride Velocity Left Hind (cm/s) | 1.974 | 2.062 | 2.054 | 2.066 | 2.242 | 2.442 |
| Stride Velocity Right Hind (cm/s) | 1.915 | 2.057 | 2.027 | 2.009 | 2.232 | 2.377 |

The biological age of each of the Labrador Retriever-like companion animals is determined by utilizing the chronological age of each of the Labrador Retriever-like companion animals to determine which biological age equation from Example 2 to use in the determination of the biological age of each of the Labrador Retriever-like companion animals. Companion Animal #1 chronological age is 3 and therefore the averages of the movement data of Companion Animal #1 is inserted into the biological age equation for age <4 years of age. The biological age of Companion Animal #1 is 3.03 years of age. Companion Animal #2 chronological age is 3 and therefore the averages of the movement data of Companion Animal #2 is inserted into the biological age equation for age <4 years of age. The biological age of Companion Animal #2 is 3.03 years of age.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of determining a companion animal's biological age, said method comprising the steps of:
   providing at least one pressure detection unit having one or more pressure sensors;
   ambulating the companion animal from a first region of the pressure detection unit to a second region of the pressure detection unit to collect footfall data;
   analyzing the footfall data and converting the footfall data into movement data;

utilizing the movement data in a biological age equation from a representative class of animals, and determining a biological age for the companion animal;

wherein the biological age equation is selected from a group of two or more equations, the equations differing based at least on the chronological age of the companion animal.

2. The method of claim 1 further comprising the step of comparing the biological age to the chronological age of said companion animal.

3. The method of claim 2 further comprising the step of providing a management program recommendation for the companion animal.

4. The method of claim 1 further comprising the step of collecting medical history related to the companion animal.

5. The method of claim 1 further comprising a step of providing a personalized report to an owner, breeder, or caregiver of said companion animal.

6. The method of claim 5 wherein said personalized report comprises information selected from the group consisting of biological age of said companion animal, footfall data of said companion animal, movement data of said companion animal and combinations thereof.

7. The method of claim 1 wherein said movement data is selected from the group consisting of number of pressure sensors activated in a given paw placement, pressure peak, pressure mean, pressure time, step length, stride length, step time, stride time, swing time, stance time, distance, ambulation time, velocity, step count, cadence, step time of all four paws, step length measured individually on each leg, cycle time measured individually on each leg, stride length measured individually for each leg, stride velocity measured individually for each leg, swing percentage of cycle measured individually on each leg, swing time measured individually for each leg, stance percentage of cycle measured individually for each leg, stance time measured individually for each leg, number of pressure sensors measured individually for each leg, mean pressure, center of gravity, and combinations thereof.

8. The method of claim 1 wherein the pressure detection unit is associated with an image collector.

9. The method of claim 1 wherein the pressure detection unit is associated with a load cell.

10. The method of claim 1 wherein kinematics sensors have been placed on the companion animal.

11. A method for evaluating a companion animal's biological age with respect to a biological age of a representative class of animals, the method comprising the steps of:

providing at least one pressure detection unit comprising one or more pressure sensors;

ambulating the companion animal from a first region of the pressure detection unit to a second region of the pressure detection unit to collect footfall data;

analyzing the footfall data and converting the footfall data into movement data and utilizing the movement data in a biological age equation from a representative class of animals and determining a biological age for the companion animal; and comparing the biological age of the companion animal to an average biological age of said representative class of animals;

wherein the biological age equation is selected from a group of two or more equations, the equations differing based at least on the chronological age of the companion animal.

12. The method of claim 11 wherein said movement data is selected from the group consisting of number of pressure sensors activated in a given paw placement, pressure peak, pressure mean, pressure time, step length, stride length, step time, stride time, swing time, stance time, distance, ambulation time, velocity, step count, cadence, step time of all four paws, step length measured individually on each leg, cycle time measured individually on each leg, stride length measured individually for each leg, stride velocity measured individually on each leg, swing percentage of cycle measured individually on each leg, swing time measured individually for each leg, stance percentage of cycle measured individually for each leg, stance time measured individually for each leg, number of pressure sensors measured individually for each leg, mean pressure, center of gravity, and combinations thereof.

13. The method of claim 11 further comprising a step of providing a personalized report to an owner, a breeder or a caregiver of said companion animal.

14. The method of claim 13 wherein said personalized report comprises information selected from the group consisting of biological age of said companion animal, footfall data of said companion animal, movement data of said companion animal and combinations thereof.

15. A database comprising a biological age of at least one companion animal, said biological age determined by a method comprising the steps of:

providing at least one pressure detection unit comprising one or more pressure sensors;

ambulating the companion animal from a first region of the pressure detection unit to a second region of the pressure detection unit to collect footfall data;

analyzing the footfall data and converting the footfall data into movement data and utilizing the movement data in a biological age equation from a representative class of animals and determining a biological age for the companion animal, wherein the biological age equation is selected from a group of two or more equations, the equations differing based on the chronological age of the companion animal; and storing the biological age in the database.

16. The database of claim 15 wherein said database comprises biological age data of a representative class of animals.

17. The database of claim 15 wherein said movement data is selected from the group consisting of number of pressure sensors activated in a given paw placement, pressure peak, pressure mean, pressure time, step length, stride length, step time, stride time, swing time, stance time, distance, ambulation time, velocity, step count, cadence, step time of all four paws, step length measured individually on each leg, cycle time measured individually on each leg, stride length measured individually for each leg, stride velocity measured individually for each leg, swing percentage of cycle measured individually on each leg, swing time measured individually for each leg, stance percentage of cycle measured individually for each leg, stance time measured individually for each leg, number of pressure sensors measured individually for each leg, mean pressure, center of gravity, and combinations thereof.

18. The database of claim 15 wherein said database further comprises information selected from the group consisting of conformation data, medical history, footfall data, movement data, biological age determinations made at different times, biological age equations, management programs and combinations thereof.

19. The database of claim 15 wherein said database is associated with a publicly accessible medium.

* * * * *